US011278585B2

(12) United States Patent
Zhang et al.

(10) Patent No.: US 11,278,585 B2
(45) Date of Patent: Mar. 22, 2022

(54) METHOD FOR PREPARING FINE BAMBOO POWDER

(71) Applicant: Senlong Bio-Tech Co., Ltd., Ya'an (CN)

(72) Inventors: Ying Zhang, Hangzhou (CN); Shiyao Fu, Hangzhou (CN); Luolian Huang, Hangzhou (CN)

(73) Assignee: SENLONG BIO-TECH CO., LTD., Ya'an (CN)

( * ) Notice: Subject to any disclaimer, the term of this patent is extended or adjusted under 35 U.S.C. 154(b) by 0 days.

(21) Appl. No.: 16/759,574

(22) PCT Filed: Oct. 24, 2018

(86) PCT No.: PCT/CN2018/111523
§ 371 (c)(1),
(2) Date: May 7, 2020

(87) PCT Pub. No.: WO2019/080848
PCT Pub. Date: May 2, 2019

(65) Prior Publication Data
US 2021/0177927 A1 Jun. 17, 2021

(30) Foreign Application Priority Data
Oct. 25, 2017 (CN) .......................... 201711004411.8

(51) Int. Cl.
| | |
|---|---|
| *A61K 36/899* | (2006.01) |
| *A23L 33/22* | (2016.01) |
| *A23L 33/105* | (2016.01) |
| *A23L 33/00* | (2016.01) |
| *A23P 10/40* | (2016.01) |
| *A61P 39/06* | (2006.01) |
| *A61P 1/16* | (2006.01) |
| *A61P 37/06* | (2006.01) |
| *A61P 3/06* | (2006.01) |
| *A61P 3/10* | (2006.01) |
| *A61P 1/00* | (2006.01) |
| *A61P 19/10* | (2006.01) |
| *A23B 7/02* | (2006.01) |
| *A23B 7/06* | (2006.01) |
| *A23B 7/154* | (2006.01) |
| *A23B 7/157* | (2006.01) |
| *A23L 3/3517* | (2006.01) |
| *A23L 3/358* | (2006.01) |
| *A23L 3/54* | (2006.01) |
| *A61K 31/192* | (2006.01) |
| *A61K 31/198* | (2006.01) |
| *A61K 31/7048* | (2006.01) |
| *A61K 31/7076* | (2006.01) |

(52) U.S. Cl.
CPC .............. *A61K 36/899* (2013.01); *A23B 7/02* (2013.01); *A23B 7/06* (2013.01); *A23B 7/154* (2013.01); *A23B 7/157* (2013.01); *A23L 3/358* (2013.01); *A23L 3/3517* (2013.01); *A23L 3/54* (2013.01); *A23L 33/105* (2016.08); *A23L 33/22* (2016.08); *A23L 33/40* (2016.08); *A23P 10/40* (2016.08); *A61K 31/192* (2013.01); *A61K 31/198* (2013.01); *A61K 31/7048* (2013.01); *A61K 31/7076* (2013.01); *A61P 1/00* (2018.01); *A61P 1/16* (2018.01); *A61P 3/06* (2018.01); *A61P 3/10* (2018.01); *A61P 19/10* (2018.01); *A61P 37/06* (2018.01); *A61P 39/06* (2018.01); *A23V 2002/00* (2013.01); *A61K 2236/15* (2013.01); *A61K 2236/31* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 2008/0233242 A1* | 9/2008 | Zhang | ................ A23L 2/44 426/72 |
| 2015/0201661 A1* | 7/2015 | Heuer | ................ A23K 20/10 424/750 |

FOREIGN PATENT DOCUMENTS

| | | |
|---|---|---|
| CN | 1528197 A | 9/2004 |
| CN | 1943442 A | 4/2007 |
| | (Continued) | |

OTHER PUBLICATIONS

Office Action dated Mar. 13, 2020 in CN Application No. 201711004411.8.
Int'l Search Report dated Jan. 22, 2019 in Int'l Application No. PCT/CN2018/111523.

(Continued)

*Primary Examiner* — Ralph J Gitomer
(74) *Attorney, Agent, or Firm* — Panitch Schwarze Belisario & Nadel LLP

(57) ABSTRACT

A MATZHU is prepared by using leaves of Gramineae (Graminae) and Bambusoideae plant as raw materials. The MATZHU has a stable emerald color and an average powder particle size of 800 to 10,000 meshes. The MATZHU also has a total amount of dietary fiber of ≥60%, a content of lignin of ≥20% and a content of minerals of ≥7%. The MATZHU includes at least three or more bamboo leaf characteristic components, such as orientin, isoorientin, vitexin, isovitexin, adenosine, δ-hydroxylysine and p-coumaric acid. The method for the MATZHU preparation includes, in turn, performing blanching and color protection, drying and superfine grinding the raw materials. By utilizing the thermal stability and the light stability of the MATZHU, the MATZHU may be used as a raw food material, a functional ingredient, or a dietary supplement.

5 Claims, 10 Drawing Sheets

(56) References Cited

FOREIGN PATENT DOCUMENTS

| | | | |
|---|---|---|---|
| CN | 101049120 | A | 10/2007 |
| CN | 102187926 | A | 9/2011 |
| CN | 107811301 | A | 3/2018 |
| JP | 2010187590 | A | 9/2010 |
| JP | 201157658 | A | 3/2011 |
| JP | 2016140325 | A | 8/2016 |
| KR | 100839029 | B1 | 6/2008 |

OTHER PUBLICATIONS

Examination Report dated May 6, 2021 in IN Application No. 202037021800.
Office Action dated Aug. 3, 2021 in JP Application No. 2020543677.
Office Action dated Aug. 21, 2020 in CN Application No. 201711004411.8.
Wen Hui-liang, "Bitter Bamboo Leaf Beverage," Health Food Processing Techniques and Formulations, pp. 319-320 (translation of relevant portion) (2002).

* cited by examiner (A) Mian bamboo-MATZHU
(B) bitter bamboo-MATZHU
(C) Bashania fangiana-MATZHU
(D) Matcha (Level 1)

METHOD FOR PREPARING FINE BAMBOO POWDER

CROSS-REFERENCE TO RELATED APPLICATION

This application is a Section 371 of International Application No. PCT/CN2018/111523, filed Oct. 24, 2018, which was published in the Chinese language on May 2, 2019, under International Publication No. WO 2019/080848 A1, which claims priority under 35 U.S.C. § 119(b) to Chinese Application No. 201711004411.8, filed Oct. 25, 2017, the disclosures of which are incorporated herein by reference in their entirety.

TECHNICAL FIELD

The invention relates to the field of natural products, food raw materials, functional ingredients and dietary supplements. More specifically, it relates to MATZHU (fine powder bamboo, fine bamboo powder, MATZOO or MOZOO) products, preparation methods and uses thereof.

BACKGROUND ART

Chinese tea drinking culture can be traced back to 2700 BC. The traditional way of drinking green tea is to brew hot water and taste the tea soup. A relevant research shows that when tea is brewed with hot water, the leaching rate of tea polyphenols is 60-70%, and the leaching rate of free amino acids is about 10% higher than that of tea polyphenols, and insoluble dietary fiber cannot be leached at all. Therefore, tea powders represented by Matcha came into being and transformed "drinking tea" into "eating tea", which not only retained the nutrients and health functions of green tea to the greatest extent, but also opened up new use of green tea in the food industry.

At present, tea powders on the market are mainly divided into two categories, namely Matcha and green tea powders, which have huge price differences and uneven quality.

Matcha is a kind of ultrafine powder produced through a series of special processing processes comprising shading, steaming and stone grinding. Its average particle size is generally 800-1000 meshes, and it has an emerald color and a refreshing seaweed aroma. Brewed with a certain amount of hot water, and fully whipped, the tea soup is dark green and with a layer of white foam on the surface, the smelling of which is overflowing. The reason why Matcha has such excellent quality is that it has unique raw materials and processing methods. The whole production process needs to go through: tea tree shading, tender shoots picking, steaming, cooling, baking, screening, stone grinding and so on. Wherein, shading treatment is one of the key steps in the production of Matcha. Shading the tea tree with one bud two leaves will increase the content of chlorophyll and amino acids in the leaves, and at the same time reduce the content of astringent tea polyphenols and caffeine. Grinding method is another key factor in Matcha making. Due to unstable green color and aroma of tea leaf, the increase of heat generated by high-speed shearing during grinding will significantly affect the color and flavor of Matcha. Therefore, traditionally, stone milling is used to maintain low speed and low temperature to minimize the loss of flavor. Matcha ground with Japanese high-quality stone mill is said to have a fineness of more than 5,000 meshes, claiming that it can be directly absorbed through the skin when applied to the skin.

The production of green tea powder is much simpler than that of Matcha. For example, ultra-fine green tea powder refers to green tea powder made by ultra-fine grinding after high-temperature fixing and dehydration drying of fresh tea leaves. The preparation process includes: leaf picking, high-temperature fixing (usually using steam to kill enzymes), twisting, dehydration drying, ultra-tine grinding, etc., which does not include the shading process by tea trees, and the grinding method uses more efficient mechanical grinding. And the product generally has a particle size of between 500 and 800 meshes, and the sensory qualities such as color, aroma and fineness are nothing compared with Matcha. Therefore, the market prices of products with significant differences between Matcha and green tea powder are also very different.

Whether it is Matcha or green tea powder, it is difficult to avoid the problems of hygienic indicators (such as heavy metals and agricultural residues). At the same time, the rich nutrients contained in the tea powder are excellent conditions for the growth of microorganisms. Therefore, excessive heavy metal, pesticide residues and excessive colony counts during storage are three key factors restricting the commodities quality of Matcha/green tea powder.

Bamboo forests are natural companions for tea gardens, and the requirements for climate and soil microecology are almost identical. China is known as the "Bamboo Kingdom". According to the Eighth National Forest Resources Survey, China's existing bamboo forest area is 90.15 million mu, mainly distributed in the Yangtze River Basin and southern provinces, including Fujian, Zhejiang, Jiangxi, Hunan and Sichuan. In 2015, the output value of the bamboo industry reached 192.3 billion yuan, and it has developed into a vigorous and potential emerging industry from resource cultivation, processing and utilization to export trade, and then to bamboo forest eco-tourism. As we all know, the national treasure giant pandas depend on bamboo forests for its livelihood, and bamboo leaves are one of their most important food sources. Bamboo leaves contain a large number of biologically active substances that are beneficial to the human body, such as flavonoids, phenolic acids, terpenes, polysaccharides, adenosine, and trace elements and minerals such as organic germanium and organic silicon, which can play a role in anti-free radicals and antioxidants, anti-fatigue, enhancing immunity, regulating lipid metabolism and preventing cardiovascular and cerebrovascular diseases. Since ancient times, people in China and Southeast Asia have had the habit of eating bamboo leaves. For example, "Qian Jin Yue Ling" records that "July Bamboo Leaf Porridge is suitable for heat stroke"; and "truth-seeking herbal foundation" said that "Bamboo leaves cool the heart and relieve spleen, clear phlegm and quench thirst". The antioxidant of bamboo leaves extracted from bamboo leaves was included in the national standard GB 2760 as a food additive in 2004, and the flavonoids of bamboo leaves were also approved by the Chinese government as "new food ingredients" in 2013. At present, there are several kinds of bamboo leaf tea and instant health tea developed from bamboo leaves as raw materials on the market.

At present, the so-called "bamboo leaf powder" or "light bamboo leaf powder" seen on the market are extracts of bamboo leaves, generally water extracts, whose basic extracting method is: adding water to dry bamboo leaves to a material liquid ratio of 1:10 to 15, hot reflux extraction, concentrating the extract under reduced pressure, and then adding fillers such as dextrin, spray drying to obtain a powder (the particle size is generally less than 300 meshes).

The color can vary from light yellow to brown according to the amount of filler, and it is slightly bitter, slightly astringent, with a certain fragrance of bamboo leaves, and the main use is as a functional ingredient of health food raw materials, food or drinks.

So far, there has not been a "MATZHU" product described in the present invention at home and abroad. The technical difficulty lies in how to maintain the stable and super stable state of chlorophyll during the processing of bamboo leaves, and to make them into ultrafine powder with emerald color and delicate texture, and to overcome the problems of excessive heavy metal, pesticide residues and microbial growth of products at the same time.

SUMMARY OF THE INVENTION

The technical problem to be solved by the present invention is to provide a MATZHU (Matzhu) or Matzoo, the preparation method and use thereof, and to provide a new type of functional raw materials, ingredients and dietary supplement ingredients for the food and health care industry.

In order to solve the above technical problems, the present invention provides a MATZHU, which is prepared by using leaves of Gramineae (Graminae) and Bambusoideae plant as raw materials, and has a stable emerald color, and has an average powder particle size of 800 to 10,000 meshes (that is, $D_{50}$ is 18.0 to 1.3 μm), and has a total amount of dietary fiber of ≥60%, a content of lignin of ≥20% and a content of minerals of ≥7%, and has at least three or more bamboo leaf characteristic components;

wherein, the bamboo leaf characteristic components are orientin, isoorientin, vitexin, isovitexin, adenosine, δ-hydroxylysine and p-coumaric acid.

Wherein, the stable emerald color means that the color value of the MATZHU is between 46 and 60 in L* and between −16 and −8 in Δa*.

Wherein, the stable emerald color means that after the MATZHU is baked at a high temperature of 180° C. for 30 minutes, its color value still remains between 40 and 50 in L* and between −7 and −5 in Δa*.

Wherein, the stable emerald color means that, after the MATZHU is ultraviolet irradiated for 180 minutes, its color value still remains between −6 and −3 in Δa*.

Preferably, the stable emerald color means that the color value is between 47 and 59 in L* and between −15 and −9 in Δa*.

The measurement and definition of the color value in the present invention adopts the L*, a*, b* chromaticity system of the International Commission on Illumination (CIE), which is most widely used to measure the hue of objects, and uses the uniform color stereoscopic representation method to define all colors by the coordinates of the three axes of L*, a*, b*. L* indicates the brightness of the sample, wherein 0 is black and 100 is white. a* indicates the red-green color direction of the sample, wherein "+" value is red and "−" value is green. b* indicates the blue-yellow color direction, wherein "+" value is yellow and "−" value is blue. The Δa value represents the difference between the a* value of the sample and the reference point, and can better represent the deviation of red-green color value of the sample from the standard white.

Wherein, the source of the raw materials is fresh leaves of henon bamboo [*Phyllostachys nigra* var. *Hnonis* (Bean) Stepf ex Rendle], Zhejiang henon bamboo (*Phyllostachys meyeri* McClure), moso bamboo (*Phyllostachys heterocycla* var. *pubescens* (Mazel) Ohwi), *Neosinocalamus affinis* (*N. affinis* (Rendle) Keng f.), Mian bamboo (*B. intermedia* Hsueh et Yi), Sulfur Yu bamboo (*Yushania* Keng f.), bitter bamboo (*P. amarus* (keng) Keng f.), *Bashania fangiana* (*B. fangiana* Keng f. et Wen), *Sasa argenteastriatus* (*Pleioblastus kongosanensis f. aureostriaus*), Qing's red bamboo (*Sasa tsuboiana*) and *Indocalamus decorus*.

Preferably, the source of the raw materials is fresh leaves of henon bamboo [*Phyllostachys nigra* var. *Hnonis* (Bean) Stepf ex Rendle], Zhejiang henon bamboo (*Phyllostachys meyeri* McClure), *Neosinocalamus affinis* (*N. affinis* (Rendle) Keng f.), Mian bamboo (*B. intermedia* Hsueh et Yi), Sulfur Yu bamboo (*Yushania* Keng f.), bitter bamboo (*P. amarus* (keng) Keng f.), *Bashania fangiana* (*B. fangiana* Keng f. et Wen), Qing's red bamboo (*Sasa tsuboiana*) and *Indocalamus decorus*.

The invention also provides the preparation method for the above-mentioned MATZHU, wherein the raw materials are sequentially subjected to blanching and color protection, drying, and superfine grinding to obtain the MATZHU with an average particle size of 800-10,000 meshes;

wherein, the raw material is the leaves of Gramineae and Bambusoideae plants;

wherein, the step of blanching and color protection is as follows: putting bamboo leaves as raw materials into a color protection liquid with a temperature of 80 to 100° C., taking out after soaking, and draining;

wherein, the color protection liquid used in the blanching and color protection is a zinc sulfate aqueous solution or a zinc gluconate aqueous solution or a combination thereof, with a concentration of 0.5 to 2.0 g/100 mL.

Wherein, the step of blanching and color protection is as follows: the bamboo leaves as raw materials are put into a color protection liquid with a temperature of 85 to 95° C., taken out after soaking for 30 to 90 s, and then drained;

wherein, the material-to-liquid ratio of bamboo leaves and color protection liquid is 1 g:50 to 100 mL;

wherein, the color protection solution used in the blanching and color protection is a zinc sulfate aqueous solution or a zinc gluconate aqueous solution or a combination thereof, with a concentration of 0.5 to 2.0 g/100 mL, and its color protection mechanism is to convert the previously unstable magnesium chlorophyll into stable chlorophyll zinc salt to maintain the stable and super stable state of chlorophyll, so that the MATZHU powder can maintain a bright emerald color.

Preferably, the color protection liquid used in the blanching and color protection is a zinc sulfate aqueous solution or a zinc gluconate aqueous solution or a combination thereof, with a concentration of 0.5 g/100 mL.

Wherein, the preparation process may also include photoelectric color sorting and metal detection steps;

wherein, the drying is: drying the leaves after the blanching and color protection treatment, to a moisture content of ≤11%;

wherein, the drying is at least one of hot air drying, microwave drying, vacuum drying and freeze drying, and a combination thereof.

Preferably, the leaves after the blanching and color protection treatment are further dried to a moisture content of ≤10% before superfine grinding.

Preferably, the leaves after the blanching and color protection treatment are further dried to a moisture content of ≤7% before superfine grinding.

Preferably, the leaves after the blanching and color protection treatment are further dried to a moisture content of ≤5% before superfine grinding.

Wherein, the source of the raw materials is fresh leaves of henon bamboo [*Phyllostachys nigra* var. *Hnonis* (Bean)

Stepf ex Rendle], Zhejiang henon bamboo (*Phyllostachys meyeri* McClure), moso bamboo (*Phyllostachys heterocycla* var. *pubescens* (Mazel) Ohwi), *Neosinocalamus affinis* (*N. affinis* (Rendle) Keng f.), Mian bamboo (*B. intermedia* Hsueh et Yi), Sulfur Yu bamboo (*Yushania* Keng f.), bitter bamboo (*P. amarus* (keng) Keng f.), *Bashania fangiana* (*B. fangiana* Keng f. et Wen), *Sasa argenteastriatus* (*Pleioblastus kongosanensis f. aureostriaus*), Qing's red bamboo (*Sasa tsuboiana*) and *Indocalamus decorus*.

Preferably, the source of the raw materials is fresh leaves of henon bamboo [*Phyllostachys nigra* var. *Hnonis* (Bean) Stepf ex Rendle], Zhejiang henon bamboo (*Phyllostachys meyeri* McClure), *Neosinocalamus affinis* (*N. affinis* (Rendle) Keng f.), Mian bamboo (*B. intermedia* Hsueh et Yi), Sulfur Yu bamboo (*Yushania* Keng f.), bitter bamboo (*P. amarus* (keng) Keng f.), *Bashania fangiana* (*B. fangiana* Keng f. et Wen), Qing's red bamboo (*Sasa tsuboiana*) and *Indocalamus decorus*.

The superfine grinding is to grind the dried leaves to an average particle size of 800-10,000 meshes.

Preferably, the superfine grinding grinds the dried leaves into an average particle size of 1,000 to 3,000 meshes.

More preferably, the superfine grinding grinds the dried leaves into an average particle size of 1,500 to 2,000 meshes.

Wherein, the superfine grinding adopts high-energy nano-impact ball grinding, zirconium balls as the grinding ball, and the ball-to-material ratio is 10:1;

alternatively, the superfine grinding may also adopt air-flow grinding;

alternatively, the superfine grinding may also use air-flow grinding+high-energy nano-impact ball grinding.

For the high-energy nano-impact ball grinding, zirconium balls are used as the grinding balls, and the ball-to-material ratio is 10:1 (w/w). The superfine grinding sample material is fragments with a diameter of 0.5-1.0 cm, which is ground for 1-8 h to obtain an average particle size of 800 to 10,000 meshes.

Preferably, the preparation process specifically uses bamboo leaves as raw materials for blanching and color protection, and the color protection liquid is 0.5 to 2.0 g/100 mL of zinc sulfate aqueous solution or zinc gluconate aqueous solution or a combination thereof, and the material-liquid ratio is 1 g:50 to 100 mL. The bamboo leaves as raw materials are put into the color protection liquid with a temperature of 85 to 95° C., the blanching time of which is 30 to 90 sec; and the bamboo leaves after blanching and color protection treatment is dried to a moisture content ≤11%, cut into 0.5-1.0 cm pieces with a crusher, and color sorted to remove the leaf trays and macular leaves. Microwave drying can be further used for sterilization and dehydration to reduce the moisture content to 10% or 7% or 5% or less. High energy nano-impact grinder or air-flow grinder is used for grinding treatment, to about 300 meshes, and then a high-energy nano-impact grinder is used with a ball-to-material ratio of 10:1, the grinding time of which is 1-8 hours, and a MATZHU product with an average particle size of 800-10,000 meshes is obtained.

A more preferred preparation process is as follows: using bamboo leaves as raw materials, using 1.5 g/100 mL (15%, w/v) of zinc gluconate aqueous solution as the color protection liquid, whose material-liquid ratio is 1 g:80 mL, and putting the bamboo leaves into the color protection liquid with a temperature of 85 to 95° C. with a blanching time of 60 sec; drying the leaves after blanching and color protection treatment at 80±1° C. until the moisture content is about 10%; cutting into 0.5 to 1.0 cm of pieces with a crusher, color sorting to remove leaf trays and macular leaves, further using microwave drying for sterilization and dehydration to reduce the moisture content to 5% or less, grinding to about 300 meshes with an air-flow grinder, and then grinding with high-energy nano-impact grinder with a ball-to-material ratio of 10:1 (w/w), the grinding time of which is 1.5 h, and a MATZHU with an average particle size of 2,000 meshes is obtained.

The color protection mechanism of the MATZHU products provided by the present invention is as follows. Chlorophyll is the main substance for coloring bamboo leaves, including chlorophyll a and chlorophyll b, etc. . . . Chlorophyll is a magnesium porphyrin compound, the chemical properties of which are extremely unstable, and light, acid, alkali, oxygen, oxidant, etc. will make it decompose and fade. For example, under acidic conditions, the chlorophyll molecule easily loses the magnesium in the porphyrin ring and becomes brown pheophytin.

The ratio of chlorophyll to pheophytin is positively correlated with the color quality of bamboo leaves. At present, the commonly used green protection method in the processing of fruits and vegetables is to replace $Mg^{2+}$ with $Zn^{2+}$, $Cu^{2+}$, $Fe^{2+}$, $Ca^{2+}$, etc., thereby forming stable chlorophyll zinc, copper, iron, calcium and other compounds, so that the greenness can be preserved. However, although the substitution mechanism of the above divalent ions for $Mg^{2+}$ in the porphyrin ring is the same, the effects of greening are different. The copper salt of chlorophyll is blue, and the iron salt is red, and both the colors are not natural. The bright emerald color of the zinc salt of chlorophyll is closest to the original plant green, so it is also the most natural and ideal. In addition, from the perspective of food safety, copper is a limited element specified by the state (copper sulfate is not a food additive and has been banned from use in food in recent years); while zinc sulfate is a food additive (listed in GB2760), and zinc gluconate is a nutrient fortifier (GB14880). Therefore, using zinc sulfate and zinc gluconate as color-protecting liquids can better preserve the greenness of bamboo leaves and is safer and healthier.

The reaction process of zinc substituted chlorophyll according to the present invention is shown in FIG. 1.

When 0.5% (w/v) zinc sulfate aqueous solution is used as the color protection liquid, the suitable blanching treatment time under 80 to 100° C. (more preferably 85 to 95° C.) is 30 to 60 sec, and the resulting leaves show the most bright and emerald color. If the blanching time is too long (such as 120 sec and longer), not only the leaf color becomes significantly lighter, but also a significant decrease in the content of active ingredients (such as flavonoids, phenolic acids, triterpenes, etc.) can be detected. After extracting the leaves with different color protection time, it can be clearly seen that the extract of the samples treated by blanching for 30 sec and 60 sec are very dark in color, while the greenness of the extract treated for 120 sec is significantly lighter. The leaves protected by this color protection treatment and the resulting MATZHU have bright and emerald color, excellent light stability and thermal stability, and excellent color stability As an improvement of the preparation method for the MATZHU of the present invention: firstly, green, ecological and pollution-free natural bamboo forests are selected, and fresh leaves are picked, thus obtaining raw materials with low heavy metal content and almost zero pesticide residue. The raw material pretreatment includes: finishing, removing impurities and cleaning of fresh bamboo leaves. The process of blanching and color protection is to put the pretreated raw bamboo leaves into a color protection liquid with a temperature of 85 to 95° C., wherein the color protection liquid is zinc sulfate aqueous solution or zinc gluconate aqueous solution or a combination thereof, with a concentration of 0.5 to 2.0 g/100 mL, controlling the blanching time between 30-90 s (material-liquid ratio is 1 g:50-100 mL), then taking out and draining. The drying process is to dry the leaves after blanching and color protection treatment (the drying can be hot air drying, microwave drying, vacuum drying or vacuum freeze drying) to a moisture content of ≤11%. After grinding to 0.5 to 1.0 cm of fragments, the leaf tray and macular leaf are removed by color sorting. Microwave heating is used for further drying and sterilizing until a moisture content of ≤5%. The superfine grinding is: the dried leaves are subjected to one or more stages of grinding (a air-flow grinder and/or nano-impact grinder) to superfine powder with an average particle size of 800~10,000 meshes (preferably 1,000-3,000 meshes, more preferably 1,500 to 2,000 meshes).

In the present invention, the superfine grinding adopts high-energy nano-impact grinding, zirconium ball as the grinding ball, and the ball-to-material ratio is 10:1 (w/w). When the injection materials are fragments with a diameter of 0.5-1.0 cm, after grinding treatment for 1 to 2 hours, the average particle size can reach more than 1,000 meshes. In order to improve the efficiency and productivity of the nano-impact grinding, an ordinary ball grinder or air-flow grinder can be equipped in front to grind the materials to 100-500 meshes in advance.

As a further improvement of the preparation method for the MATZHU of the present invention, henon bamboo leaves are used as raw materials, and 1.5 g/100 mL (1.5%, w/v) of zinc gluconate aqueous solution is used as the color protection liquid, the material-to-liquid ratio of which is 1 g:80 mL, with a heat blanching time of 60 sec. The blanched and color-protected leaves are dried at 80±1° C. until a moisture content of about 10.0%, cut into 0.5 to 1.0 cm of pieces with a crusher, color sorted to remove leaf trays and macular leaves. Microwave drying is further used for sterilization and dehydration to reduce the moisture content to 5% or less. An air-flow grinder is used for grinding to about 300 meshes, and then grinding using a high-energy nano-impact grinder, with a ball-to-material ratio of 10:1 (w/w), the grinding time of which is 4 h, and a MATZHU with an average particle size of 2,000 meshes is obtained.

The present invention also provides the use of the MATZHU prepared by the above method: by using the thermal stability and light stability of the MATZHU, the MATZHU is used as food raw materials, functional ingredients, or as a dietary supplement;

wherein, the added amount of MATZHU is 1-10% (w/w), preferably 2-5% (w/w).

Improvements of the use of the MATZHU of the present invention include any one of the following:

stable natural green pigment;

supplementing human dietary fiber, improving gastrointestinal function, helping to control weight and prevent constipation;

improving and regulating intestinal flora, increasing the body's sensitivity to insulin, preventing and treating insulin resistance, and preventing metabolic syndrome;

strengthening natural antioxidant components such as bamboo leaf flavonoids, p-coumaric acid, adenosine, and δ-hydroxylysine etc. helping to improve the human microcirculation, regulating the metabolism of glycolipids, and effectively protecting the cardio and cerebral vessels; and providing abundant minerals and trace elements, especially bamboo-specific ingredients such as organic silicon and organic germanium etc., helping to prevent osteoporosis, maintaining skin youthfulness, and delaying human aging.

The invention uses fresh bamboo leaves as raw materials and adopts unique processing technology to create an superfine powder with excellent emerald color, delicate smell and uniform fineness, which is called MATZHU, and has the processing suitability and health effect close to matcha, thus providing a new type of natural, green food functional ingredients and/or dietary supplements rich in bamboo leaf chemicals and dietary fiber for the human society.

The MATZHU of the invention has a bright emerald color, with high thermal stability and light stability, and can be widely used in the food industry as a coloring agent, a thickening agent and a flavoring agent, such as cakes, cookies, ice cream, chocolate, candy and milk tea, and is more advantageous especially in foods that require high-temperature processing (such as baking, frying, puffing). In addition, MATZHU can be used independently as a dietary supplement, and can also be used in pet food or livestock and aquatic feed.

The MATZHU of the present invention is used as a food material of natural origin and a functional ingredient with low energy density in various food systems.

The MATZHU of the present invention has significantly lower heavy metal (lead, arsenic, mercury, cadmium, etc.) contents and pesticide residues than those of matcha.

The MATZHU of the present invention with different particle size distributions can be obtained by selecting different grinding equipment or a combination thereof and adjusting the process parameters of the grinding unit.

The beneficial effects of the present invention are prominently as follows: firstly, according to the characteristics of bamboo leaf materials (high fiber content, with effective ingredients not easy to dissolve: emerald color, good thermal stability, etc.), hot water bleaching method is used, a zinc salt solution is used for replacement color protection treatment, that is, the unstable magnesium chlorophyll salt in the original leaf is converted into a highly stable zinc chlorophyll salt to maintain its emerald color. Secondly, based on the stability of the above raw materials, high-energy nano-impact grinder is used to achieve the superfine grinding of bamboo leaves. Compared with the matcha process using stone grinding, the production efficiency of the grinding step is greatly improved. At the same time, the high-strength zirconium balls used in the crushing (grinding) process can also ensure that foreign substances in the MATZHU are avoided (and it is difficult to prevent stone powder from entering into the product during stone grinding). Thirdly, most of the bamboo forests in China are natural forests or semi-natural forests where pesticides and chemical fertilizers are rarely used, which is conducive to the production of natural, green, and pollution-free organic MATZHU products.

The MATZHU of the present invention has the following specific uses:

1) as a natural source of fibrous food ingredients and low energy density functional ingredients, MATZHU can be used in solid, semi-solid, and suspended foods to supplement human dietary fiber and improve gastrointestinal function, and help to prevent constipation and control weight.

2) due to the emerald appearance, fragrance flavor and good color stability of MATZHU, it can be used as a natural colorant, thickener and flavoring agent in all food fields where MATZHU may be used (such as cakes and cookies, ice cream, chocolate, candy, milk tea, coffee, etc.), especially in high-temperature processed food systems (such as baked, fried, extruded and expanded products).

3) when added to various foods in a certain proportion, MATZHU helps to improve and regulate the intestinal flora, increase the body's sensitivity to insulin, prevent and treat insulin resistance, and prevent metabolic syndrome.

4) when added to various foods in a certain proportion, MATZHU strengthens natural antioxidant components such as bamboo leaves flavonoids and polyphenols, and can improve the human microcirculation, regulate lipid metabolism, and effectively protect the cardio and cerebral vessels.

5) when added to various foods in a certain proportion, MATZHU strengthens bamboo's unique organic silicon, organic germanium and other ingredients, helps prevent osteoporosis, keeps the skin young and delays human aging.

In addition, the MATZHU of the present invention can be eaten independently as a dietary supplement, and can also be applied to pet food or added to livestock, poultry and aquatic feed.

Compared with the prior art, the present invention has the following main advantages:

1) Using bamboo leaves as a raw material, the inventors have invented a MATZHU with stable emerald color, fragrance smell and uniform fine powder. Compared with the production of matcha, the process herein is simple and the material is convenient. Due to the special texture of bamboo leaves (its degree of fiberization is higher than that of tea leaves) and the high stability of chlorophyll zinc salt after color protection treatment, a product with different fineness and an average particle size of 800-10,000 meshes (i.e. $D_{50}$ is between 18 and 1.3 μm) can be obtained by using different degrees of mechanical crushing.

2) The MATZHU of the present invention has a total dietary fiber of >60%, a lignin content of >20% and minerals (ash) content of >7%, all of which are equal to or higher than that of matcha. At the same time, it is rich in specific functional components of bamboo leaves such as c-glycosyl flavone (orientin, isoorientin, vitexin, isovitexin), adenosine, δ-hydroxylysine, p-coumaric acid, organic germanium and organic silicon.

3) The MATZHU of the present invention is brighter and greener than matcha, and has higher thermal stability and light stability. Under a baking temperature of 180° C., the MATZHU basically remained green for 30 minutes, while the matcha had browned significantly at 15 minutes. Due to its green and stable natural color, MATZHU can be directly added as a natural pigment to various solid, semi-solid and suspended foods that need to be colored. For example, it is used in cakes, cookies, ice cream, chocolate, candy, milk tea and coffee, especially in foods that require high temperature processing (such as baking, frying, puffing). At the same time, it can also play a role in thickening and flavoring in the food systems.

4) Due to its rich fiber, minerals and various bamboo leaf active ingredients, as a natural source of food and low energy density functional ingredient, it can be used in various foods to supplement dietary fiber for human body and improve gastrointestinal function, etc., and it helps to control weight and prevent constipation; and it helps to improve and adjust the intestinal flora, increase the body's sensitivity to insulin, prevent and treat insulin resistance, and prevent metabolic syndrome, and it helps to improve human microcirculation, regulate sugar and lipid metabolism, effectively protect cardio and cerebral vessels; and it helps to prevent osteoporosis, keep skin young and delay human aging.

5) Pure natural bamboo forests or semi-natural wood forests with good site conditions are hardly administered fertilizers or pesticides. Due to this innate advantage, MATZHU has a heavy metal level much lower than Matcha and is with almost no pesticide residues, and is a substantially pure natural green organic food. The presence of special bacteriostatic components (flavonoids, phenolic acids, etc.) in bamboo leaves and relatively low content of conventional nutrients (such as protein, amino acids, sugar, etc.), as well as the relatively high heat intensity produced during microwave radiation and high-speed shearing make the total number of colonies of MATZHU products much lower than that of matcha, and it is easier to control the microbial indicators during the circulation of commodities.

Bamboo forests in China are mainly distributed in the old revolutionary base areas, regions inhabited by ethnic groups, border and outlying areas and poor areas. The invention of MATZHU opens a new way for the high-value transformation of bamboo resources. While providing high-quality food functional ingredients and dietary supplements for human society and promoting the construction of a healthy China, it also greatly contributes to the solution of the "three rural" issues and the poverty alleviation of the poor, and it will surely become a new economic growth point for the bamboo industry.

DESCRIPTION OF FIGURES

The specific embodiments of the present invention will be further described in detail below with reference to the drawings.

In each column, they are Firmicutes, Bacteroidetes, Actinobacteria, Proteobacteria, and Verrucomicrobia from the bottom to the top in turn.

Figure 12:
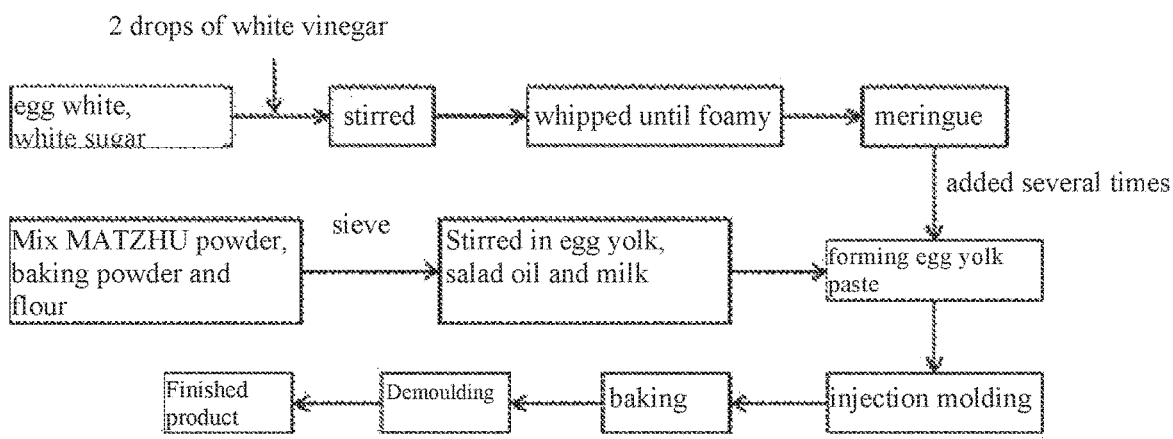

FIG. 12 shows a process flow chart of cake making.

Figure 13:
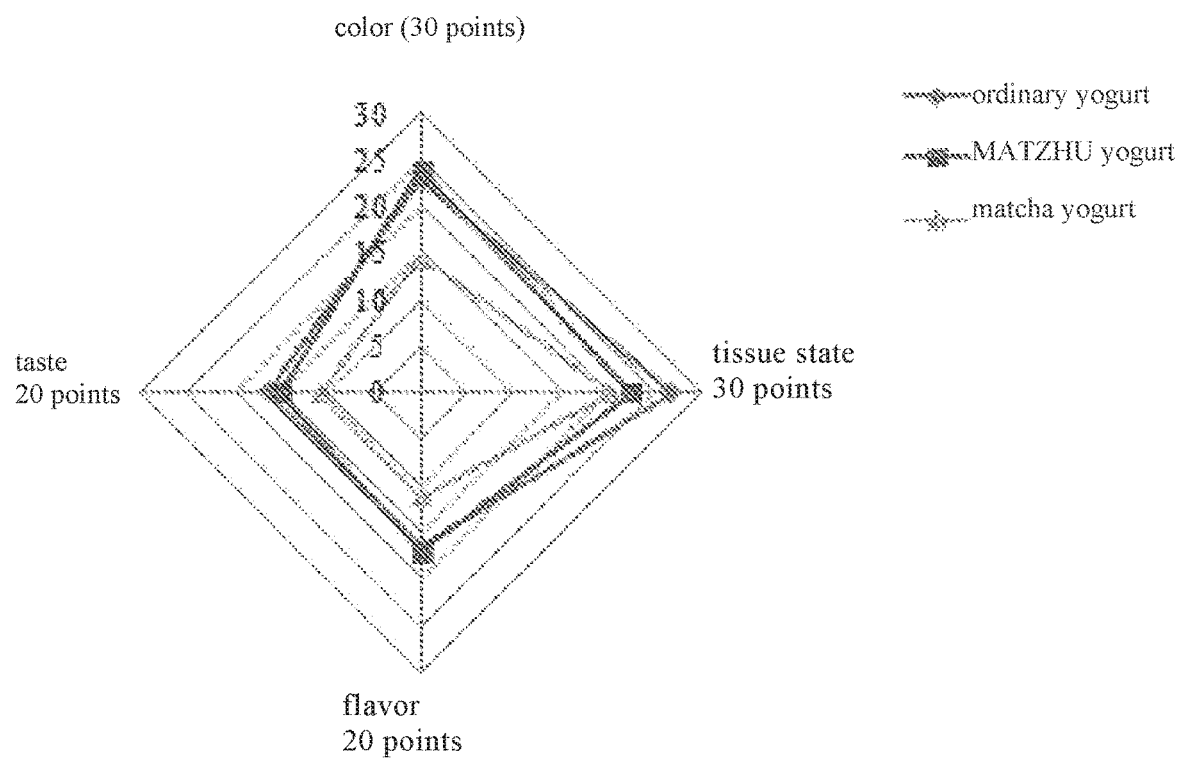

FIG. 13 shows sensory evaluations of three yogurts: plain yogurt and two yogurts added with the same ratio of MATZHU (Example 1.5) and matcha, respectively.

Figure 14:
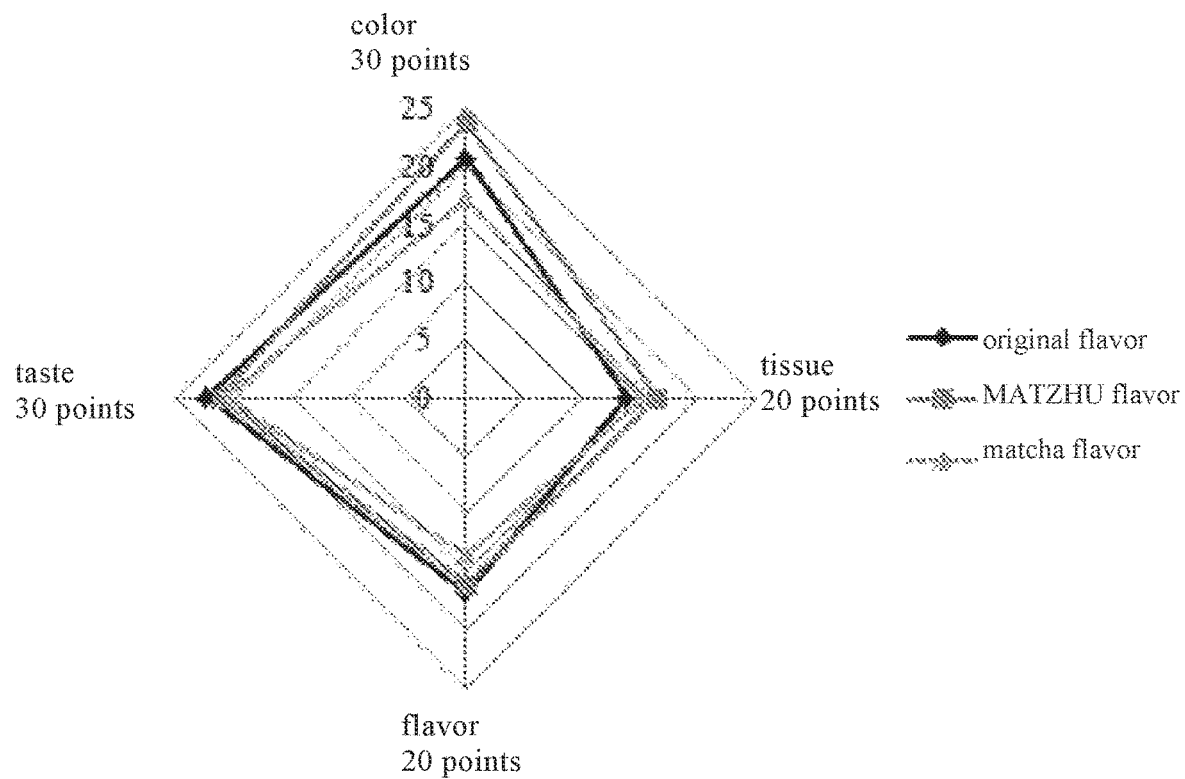

FIG. 14 shows sensory evaluations of three nougats blank control, nougat added with MATZHU as described in Example 1.5, and nougat added with matcha.

DETAILED DESCRIPTION OF THE INVENTION

The present invention is further elaborated below in conjunction with specific examples. The examples are only for illustrating the present invention and should not limit the scope of the present invention. Where no specific technology or conditions are indicated in the examples, the technical conditions described in the relevant literature in the art are used. The reagents used, which do not indicate the manufacturer, are commonly used experimental reagents and products.

Unless otherwise defined, all professional and scientific terms used in the text have the same meanings as known to the skilled in the art. In addition, any methods and materials similar or equal with the recorded content can be applied to the methods of the invention. The methods and materials in the preferred embodiment described herein are only for demonstration purposes.

The raw materials of the present invention are: preferably fresh leaves with complete forms, from which old, yellow leaves and insect spot leaves are removed, and the petioles are removed as much as possible; most preferably bamboo cores that have not yet exhibited leaves, which can be used to prepare superb MATZHU.

The MATZHU described in the present invention is prepared by using leaves of Gramineae (Graminae) and Bambusoideae plant as raw materials, and has a stable emerald color, and has an average powder particle size of 800 to 10,000 meshes (that is, $D_{50}$ is 18 to 1.3 μm), and has a total amount of dietary fiber of ≥60%, a content of lignin of ≥20% and a content of minerals of ≥7%, and has at least three or more bamboo leaf characteristic components;

wherein, the bamboo leaf characteristic components are orientin, isoorientin, vitexin, isovitexin, adenosine, δ-hydroxylysine and p-coumaric acid.

Wherein, the stable emerald color means that the color value of the MATZHU is between 46 and 60 in L* and between −16 and −8 in Δa*.

Wherein, the stable emerald color means that after the MATZHU is baked at a high temperature of 180° C. for 30 minutes, its color value still remains between 40 and 50 in L* and between −7 and −5 in Δa*.

Wherein, the stable emerald color means that, after the MATZHU is ultraviolet irradiated for 180 minutes, its color value still remains between −6 and −3 in Δa*.

Preferably, the stable emerald color means that the color value is between 47 and 59 in L* and between −15 and −9 in Δa*.

The preparation method of MATZHU is as follows:

1) Picked fresh bamboo leaves are subjected to blanching and color protection after being selected and decontaminated. The color protection solution is 0.5 to 2.0 g/100 mL of any one of zinc sulfate or zinc gluconate aqueous solution and a combination thereof. The bamboo leaves as raw materials are put into a color protection liquid with a temperature of 85 to 95° C., taking out after soaking for 30 to 90 s, and then drained. The material-to-liquid ratio of the bamboo leaves to the color protection liquid is 1 g:50 to 100 mL.

2) Dry the leaves after blanching, color protection and draining to reduce the moisture content of the leaves to less than 11.0%, wherein the method can be any one of hot air drying, microwave drying, vacuum drying, freeze drying and a combination thereof.

3) Grind the dried leaves into pieces with a diameter of about 0.5 to 1.0 cm, using photoelectric color sorter to remove leaf trays, macular leaves, etc., to further improve its purity. Then by using microwave heating, while performing sterilization treatment, the leaf moisture is reduced to 5% or below.

4) Superfine grind the dried bamboo leaves, using high-energy nano-impact ball grinder, wherein the grinding ball is a zirconium ball, with a ball-to-material ratio of 10:1 (w/w). The superfine grinding sample material is pieces with a diameter of 0.5 to 1.0 cm, ground for 1-8 hours to obtain fine uniform superfine powder of MATZHU with an average particle size of 800-10,000 meshes, with a bright emerald color and a fresh fragrance. Prior to superfine grinding, it can be ground step by step. The grinding equipment can be any one of ball mill, stone mill, high-energy nano-impact mill and jet mill and a combination thereof.

The test method adopted by the present invention is as follows:

1. Color Difference Analysis

Testing instrument: Colorimeter CM-600d (produced by KNICA MINOLTA, Japan).

Experimental method steps: firstly, zero-calibrating the colorimeter on the whiteboard, and then taking a certain amount of MATZHU samples onto a standard whiteboard, and evenly spreading the samples, and aligning the light inlet of the colorimeter with the sample, and then clicking the test button to test.

The measurement principle of the portable colorimeter used for food evaluation adopts the $L^*$, $a^*$, $b^*$ chromaticity system of the International Commission on Illumination (CIE), which is most widely used to measure the hue of objects, and uses the uniform color stereoscopic representation method to define all colors by the coordinates of the three axes of $L^*$, $a^*$, $b^*$. $L^*$ indicates the brightness of the sample, wherein 0 is black and 100 is white. $a^*$ indicates the red-green color direction of the sample, wherein "+" value is red and value is green. $b^*$ indicates the blue-yellow color direction, wherein "+" value is yellow and "−" value is blue. The $\Delta a$ value represents the difference between the $a^*$ value of the sample and the reference point, and can better represent the deviation of red-green color value of the sample from the standard white.

2. Particle Size Measurement

Detection instrument: LS-230 Coulter laser particle size analyzer (produced by Coulter Corporation, US).

Experimental method steps: using distilled water as the dispersion medium, weighing a certain amount of powder sample and adding it into water, and ultrasonically dispersing for 1 min; turning on the laser particle size analyzer in advance to preheat it, and washing the instrument with absolute ethanol and distilled water in sequence until PIDS=0~2%; opening the sample inlet, and then slowly dropping the dispersed sample solution into the laser particle size analyzer; when the instrument displays PIDS=40% (or the test solution concentration reaches 8%), clicking the test button to test.

3. Determination of total flavonoid content (aluminum nitrate-sodium nitrite colorimetric method, with rutin as a standard product)

This method refers to "Testing Methods for Effective Ingredients of Health Foods" edited by Wang Guangya (China Light Industry Press, 2002, p 29-31).

1) Standard Curve Production

Precisely weighing 10 mg of rutin as a standard and adding it into 100 mL flask, adding methanol to dissolve and diluting to the mark, drawing 0, 0.5, 1.0, 2.0, 3.0, 4.0 mL of solution therefrom into 25 mL colorimetric tube, adding 30% ethanol solution to dilute the solution to 5 mL, adding 0.3 mL of 5% sodium nitrite solution in turn, and placed for 5 min after shaking; adding 0.3 mL of 10% aluminum nitrate solution, and placed for 6 min after shaking; adding 4.0 mL of 1.0 mol/L sodium hydroxide solution, diluting with 30% ethanol solution to 10.0 mL, placed for 10 min after shaking; taking the No. 0 tube as a blank, shaking and measuring the absorbance at a wavelength of 510 nm with a 1 cm cuvette, drawing a standard curve with the absorbance as the vertical ordinate and the concentration as the horizontal ordinate.

2) Determination of the Total Flavonoid Content of the Sample

Accurately weighing the appropriate amount of the sample, adding 70% ethanol at a material-to-liquid ratio of 1:20, extracting with hot reflux in water bath at 90° C. for 2 h, and filtering the extract to a fixed volume, then measuring the flavonoid content in the extract according to the same method as described in the preparation of the standard curve, and then converting it into the total flavonoid content of the MATZHU.

4. Determination of total phenol content (Folin reagent reduction colorimetry, with p-hydroxybenzoic acid as a standard product)

1) Standard Curve Production

Precisely weighing 25.0 mg of p-hydroxybenzoic acid as a standard after vacuum dried to constant mass, dissolving in water and diluting to 100 mL flask to make 0.250 mg/mL of p-hydroxybenzoic acid standard solution; accurately drawing 0.05, 0.10, 0.20, 0.40, 0.80, 1.20 mL of the standard solution, transferring them into 25 mL stopper test tubes, and diluting to 10.0 mL with water respectively; adding 1.0 mL of Folin reagent diluted twice and 2.0 mL of 20% $Na_2CO_3$ aqueous solution, heating on a boiling water hath for 1 min, cooling with water and dilute to 25 mL; placing at room temperature for 30 min, and measuring the absorbance at a wavelength of 745 nm; and drawing a standard curve with absorbance as the vertical ordinate and concentration of p-hydroxybenzoic acid as the reference substance as the horizontal ordinate.

2) Determination of Total Phenol Content of the Sample

Accurately weighing the appropriate amount of the sample, adding 70% ethanol at a material-to-liquid ratio of 1:20, extracting with hot reflux in water bath at 90° C. for 2 h, and filtering the extract to a fixed volume; then measuring the total phenol content of the extract according to the same method described in the preparation of the standard curve, and then converting into the total phenol content of the MATZHU.

5. Determination of total triterpene saponin content (vanillin-glacial acetic acid colorimetric method, arbutin as standard product)

1) Standard Curve Production

Transferring 20 mg of arbutin standard product into a small beaker, dissolving with 95% ethanol, diluting to 100 mL, shaking well to obtain 0.200 mg/mL ursolic acid standard solution; Transferring 0.0, 0.5, 1.0, 1.5, 2.0, 2.5 and 3.0 mL standard solutions into 8 test tubes respectively and placing in 85° C. water bath to evaporate ethanol: adding 0.5 mL of 5% vanillin-glacial acetic acid solution respectively and shaking well, adding 1.0 mL perchloric acid respectively, and shaking well; after reacting in a 60° C. water bath for 15 minutes, taking it out for cooling; adding 5.0 mL of 4% glacial acetic acid, shaking well, and measuring the absorbance at a wavelength of 548 nm; making the standard curve with the concentration (μg/mL) as the vertical ordinate and the absorbance as the horizontal ordinate.

2) Determination of Total Triterpene Content of the Sample

Taking 5.0 g of MATZHU, adding 100 mL of methanol, extracting under hot reflux in a water bath at 75° C. for 2 h, filtering, spin dry, adding water to disperse; extracting 5 times with n-butanol with a volume ratio of 1:1, combining n-butanol phase, spin dry, adding water and spinning to be tasteless; dissolving with methanol and diluting to 250 mL; then, determining the triterpene saponin content of the MATZHU extract according to the method described in the preparation of the standard curve, and then converting into the total triterpene saponin content of the MATZHU.

EXAMPLE 1

Preparation of MATZHU 1.1 Using Henon Bamboo Leaves as a Raw Material

1) The picked fresh henon bamboo leaves were screened to remove branches, old leaves, yellow leaves and speckled leaves, and the petioles were removed as much as possible 2) After cleaned, the leaves were treated with blanching and color protection. The color protection liquid was 1.5% (w/v) of zinc gluconate aqueous solution, and the material-to-liquid ratio was 1 g:80 mL (w/v). According to the above material-to-liquid ratio, a certain amount of henon bamboo fresh leaves were put into the slightly boiling color protection liquid (that is, the color protection liquid was heated to 85 to 90° C.), gently stirred to evenly disperse the leaves, quickly removed after 60 sec, drain to dry.

3) The blanched bamboo leaves were put into an oven for drying, with a drying temperature of (80±1)° C., the time of which was 1.5 h, then cooled to room temperature, thus obtaining dried leaves with a moisture content of about 10%.

4) The dried leaves were cut into 0.5-1.0 cm of fragments with a crusher, and after color selection, the leaf trays and macular leaves were removed. Microwave drying was further used for sterilization and dehydration to reduce the moisture content to 5% or less.

5) The bamboo leaves were grinded using a air-flow grinder to about 300 meshes, and then a high-energy nano-impact grinder (produced by Qinhuangdao Taijihuan Nano Products Co., Ltd., model CJM-SY-B; the below was the same) was used for crushing treatment, with a ball-to-material ratio of 10:1 (w/w) and a ball grinding time of 1.0 h, thus obtaining the MATZHU with an average particle size of about 900 meshes (recorded as: henon bamboo-MATZHU).

The color, particle size and content of biologically active substances were measured. The results are shown in Table 1.

TABLE 1

| | Product characteristics of henon bamboo-MATZHU | | | | | |
|---|---|---|---|---|---|---|
| | | | particle | biologically active substances % | | |
| Related | color values | | size | total | total | total |
| parameters | L* | Δa* | $D_{50}$/μm | flavonoids | phenol | triterpenes |
| henon bamboo-MATZHU | 50.32 ± 0.42 | −10.48 ± 0.05 | 16.86 | 2.81 ± 0.38 | 3.33 ± 0.25 | 2.39 ± 0.58 |

1.2 Using *Neosinocalamus affinis* Leaves as a Raw Material

1) The picked fresh *Neosinocalamus affinis* leaves were picked to remove old leaves, yellow leaves and speckled leaves, and the petioles were removed as much as possible.

2) After washed, blanching and color protection treatment were carried out. The color protection liquid was 0.5 g/100 mL (0.5%, w/v) of zinc gluconate aqueous solution, with a material-to-liquid ratio of 1 g:80 mL (w/v). According to the above material-to-liquid ratio, a certain amount of *Neosinocalamus affinis* fresh leaves were put into the slightly boiling color protection liquid (that is, the color protection liquid was heated to 85 to 90° C.), gently stirred to evenly disperse the leaves, quickly removed after 90 sec, drain to dry.

3) The blanched bamboo leaves were put into an oven for drying, with a drying temperature of (80±1)° C. and a drying time of 1.5 h, cooled to room temperature, thus obtaining dried leaves with a moisture content of about 10%.

4) The dried leaves were cut into 0.5-1.0 cm of fragments, and after color selection, the leaf trays and macular leaves were removed. Microwave drying was further used for sterilization and dehydration to reduce the moisture content to 5% or less.

5) The high-energy nano-impact grinder was used to crush the dried bamboo leaves with a ball-to-material ratio of 10:1 (w/w) and a ball grinding time of 30 minutes. The MATZHU with an average particle size of about 900 meshes was obtained (recorded as: *Neosinocalamus affinis*-MATZHU).

The color, particle size and content of biologically active substances were measured. The results are shown in Table 2.

TABLE 2

Product characteristics of Neosinocalamus affinis-MATZHU

| Related parameters | color values L* | Δa* | particle size $D_{50}/\mu m$ | biologically active substances % total flavonoids | total phenol | total triterpenes |
|---|---|---|---|---|---|---|
| Neosinocalamus affinis-MATZHU | 47.03 ± 0.71 | −8.31 ± 0.09 | 16.06 | 3.21 ± 0.40 | 3.48 ± 0.55 | 2.44 ± 0.25 |

1.3 Using Mian Bamboo Leaves as a Raw Material

1) The freshly picked Mian bamboo leaves were screened to remove old leaves, yellow leaves and speckled leaves, and the petioles were removed as much as possible.

2) Blanching and color protection treatment were carried out, wherein the color protection liquid adopted 1.0% (w/v) of zinc sulfate aqueous solution, and the material-liquid ratio was 1 g:80 mL (w/v). According to the above material-liquid ratio, a certain amount of Mian bamboo leaves was added to the slightly boiling color protection liquid (that is, the color protection liquid was heated to 85-95° C.), and gently stirred to evenly disperse the leaves, quickly removed after 30 sec and drain to dry.

3) The blanched bamboo leaves were put in a vacuum drying oven (vacuum degree was about 100±10 Pa, drying temperature was about 40° C., drying time was 150 min) to obtain dried leaves with moisture content of 4.5%.

4) Use high-energy nano-impact mill to treat the dried Mian bamboo leaves with a ball-to-material ratio of 15:1 (w/w) and a crushing time of 2 hours to obtain a MATZHU with an average particle size of about 2000 mesh (recorded as: Mian bamboo-MATZHU).

The color, particle size and content of biologically active substances were measured. The results are shown in Table 3.

1.4 Using Sulfur Yu Bamboo Leaves as a Raw Material

1) The picked fresh Sulfur Yu bamboo leaves were screened to remove old leaves, yellow leaves and speckled leaves, and the petioles were removed as much as possible.

2) Blanching and color protection treatment were carried out. The green protection liquid was 2% (w/v) of zinc gluconate aqueous solution, and the material-liquid ratio is 1 g:80 mL (w/v). According to the above material-to-liquid ratio, a certain amount of fresh bamboo leaves was put into the slightly boiling color protection liquid (that is, the color protection liquid was heated to 85 to 95° C.), gently stirred to evenly disperse the leaves, quickly removed after 90 sec, drain to dry.

3) The drained bamboo leaves were continuously processed with a belt microwave drying equipment (Shanghai Yuanyue Light Industry Machinery Co., Ltd., model YTLD) with a microwave power of 4 Kw and a conveyor belt speed of about 0.5 m/min and a drying time of about 60 minutes to get dried leaves with a moisture content of about 7%. And then the dried leaves were broken into pieces by using an ordinary Chinese herbal medicine crusher, and for later use.

4) The above pieces were treated with airflow crushing equipment (Weifang Zhengyuan Powder Engineering Equipment Co., Ltd., model: LHJ-10 laboratory ultrafine

TABLE 3

Product characteristics of Mian bamboo-MATZHU

| Related parameters | color values L* | Δa* | particle size $D_{50}/\mu m$ | biologically active substances % total flavonoids | total phenol | total triterpenes |
|---|---|---|---|---|---|---|
| Mian bamboo-MATZHU | 53.44 ± 0.92 | −13.78 ± 0.07 | 6.976 | 2.35 ± 0.15 | 3.26 ± 0.27 | 2.50 ± 0.75 | mechanical crusher) to obtain powder with an average particle size of about 800 meshes (recorded as: Sulfur Yu bamboo-MATZHU).

The color, particle size and content of biologically active substances were measured. The results are shown in Table 4.

TABLE 4

Product characteristics of Sulfur Yu bamboo-MATZHU

| Related parameters | color values | | particle size | biologically active substances % | | |
|---|---|---|---|---|---|---|
| | L* | Δa* | $D_{50}$/μm | total flavonoids | total phenol | total triterpenes |
| Sulfur Yu bamboo-MATZHU | 58.69 ± 0.56 | −11.09 ± 0.04 | 18.09 | 1.97 ± 0.758 | 2.89 ± 0.11 | 1.37 ± 0.25 |

1.5 Using Bitter Bamboo Leaves as a Raw Material

1) The picked fresh bitter bamboo leaves were screened to remove old leaves, yellow leaves and speckled leaves, and the petioles were removed as much as possible.

2) Blanching and color protection treatment were carried out, wherein the color protection liquid adopted 0.5% (w/v) of zinc sulfate aqueous solution, and the material-liquid ratio was 1 g:80 mL (w/v). According to the above material-to-liquid ratio, a certain amount of bitter bamboo leaves were put into the slightly boiling color protection liquid (that is, the color protection liquid was heated to 85 to 95° C.), gently stirred to evenly disperse the leaves, quickly removed after 60 sec, drain to dry.

3) The blanched bitter bamboo leaves were put into the hot air drying oven with a drying temperature of (80±1)° C. and a drying time of 1.5 h to obtain dried leaves with a moisture content of 5.0%.

4) The high-energy nano-impact grinder was used for crushing treatment. The ball-to-material ratio was 10:1 (w/w) and the crushing time was 3 h. The MATZHU with an average particle size of about 8000 meshes was obtained (recorded as: bitter bamboo-MATZHU). Product characteristics are shown in Table 5.

1.6 Using *Bashania fangiana* Leaves as a Raw Material

1) The picked fresh *Bashania fangiana* leaves were screened to remove old leaves, yellow leaves and speckled leaves, and the petioles were removed as much as possible.

2) Blanching and color protection treatment were carried out, wherein the color protection liquid adopted 0.5% (w/v) of zinc sulfate aqueous solution, and the material-liquid ratio was 1 g:80 mL (w/v). According to the above material-to-liquid ratio, a certain amount of *Bashania fangiana* leaves were put into the slightly boiling color protection liquid (that is, the color protection liquid was heated to 85 to 95° C.), gently stirred to evenly disperse the leaves, quickly removed after 30 sec, drain to dry.

3) The drained bamboo leaves were put into the hot air drying oven with a drying temperature of (80±1)° C. and a drying time of 1.5 h to obtain dried leaves with a moisture content less than 5%.

4) The high-energy nano-impact grinder was used for crushing treatment. The ball-to-material ratio was 10:1 (w/w) and the crushing time was 2 h. The MATZHU with an average particle size of about 10,000 meshes was obtained (recorded as: *Bashania fangiana*-MATZHU).

TABLE 5

Product characteristics of bitter bamboo-MATZHU

| Related parameters | color values | | particle size | biologically active substances % | | |
|---|---|---|---|---|---|---|
| | L* | Δa* | $D_{50}$/μm | total flavonoids | total phenol | total triterpenes |
| bitter bamboo-MATZHU | 55.74 ± 0.48 | −15.36 ± 0.04 | 1.58 | 2.44 ± 0.39 | 3.10 ± 0.11 | 2.22 ± 0.29 |

Product characteristics are shown in Table 6.

TABLE 6

Product characteristics of Bashania fangiana-MATZHU

| Related parameters | color values | | particle size | biologically active substances % | | |
|---|---|---|---|---|---|---|
| | L* | Δa* | $D_{50}/\mu m$ | total flavonoids | total phenol | total triterpenes |
| Bashania fangiana-MATZHU | 56.47 ± 0.12 | −13.28 ± 0.07 | 1.145 | 1.94 ± 0.1.8 | 3.93 ± 0.42 | 1.92 ± 0.27 |

1.7 Detection of the Characteristic Components of MATZHU

The appropriate amount of the above six MATZHU samples were taken to determine the contents of the bamboo leaf characteristic components.

Preparation of sample solutions: taking a certain amount of MATZHU and adding 30% ethanol solution at a material-to-liquid ratio of 1:20; then extracting in a water bath at 70° C. for 2 h; filtering and retaining the extract, concentrating it in vacuum and transferring to a 50 mL flask, dissolving with methanol to a fixed volume; storing at 4° C., filtering the samples through 0.22 μm microporous membranes before injection, and taking the filtrate as the test solutions for future use.

The determination methods for bamboo leaf c-glycosyl flavone (orientin, isoorientin, vitexin, isovitexin) and p-coumaric acid refer to the national standard "food additives bamboo leaf antioxidants" (GB 30615-2014). The chromatographic conditions were: $C_{18}$ ODS column (4.6 mm×250 mm, 5 μm); mobile phase mixed solvent A (acetonitrile) and solvent B (acetic acid solution with a volume fraction of 0.2%). Gradient elution conditions were: 0 to 15 min, A 15%, B 85%, 15 to 25 min, A 15% to 40%, B 85% to 60%; 25 to 34 min, A 40%, B 60%; 34 to 40 min, A 40% to 15%, B 60% to 85%; flow rate 1.0 mL/min; detection wavelength 330 nm; column temperature 30° C.; injection volume 10 μL.

δ-hydroxylysine was measured with an automatic amino acid analyzer (Hitachi 835-50 high-speed automatic amino acid analyzer), wherein the standard product was from Wako Pure Chemical Industries, Ltd., Japan. The determination of adenosine refers to the reference [Gong Jinyan, et al., HPLC Method for determination of adenosine content in bamboo shavings extract and its different parts, Food Industry 2014, 35 (12): 264-265], wherein the standard product was from China National Institute for the Control of Pharmaceutical and Biological Products.

The test results of the characteristic components of six kinds of MATZHU samples are shown in Table 7.

TABLE 7

Characteristic components of bamboo leaves contained in MATZHU from different bamboo leaf varieties [μg/g on a dry basis]

| Characteristic components | henon bamboo-MATZHU | Neosinoca lamus affinis-MATZHU | Mian bamboo-MATZHU | Sulfur Yu bamboo-MATZHU | bitter bamboo-MATZHU | Bashania fangiana-MATZHU |
|---|---|---|---|---|---|---|
| orientin | 287 | 233 | 115 | ND | 228 | 189 |
| isoorientin | 336 | 305 | 184 | 195 | 241 | 219 |
| vitexin | 215 | 208 | 113 | 129 | 279 | 268 |
| isovitexin | 263 | 290 | 204 | 170 | 189 | 158 |
| p-cournaric acid | 276 | 218 | 161 | 187 | 203 | 192 |
| δ-hydroxylysine | 1104 | 1010 | 998 | 890 | 1500 | 1200 |
| adenosine | 2.5 | 2.1 | 1.5 | 1.7 | 1.8 | 2.3 |

EXAMPLE 2

Figure 1:
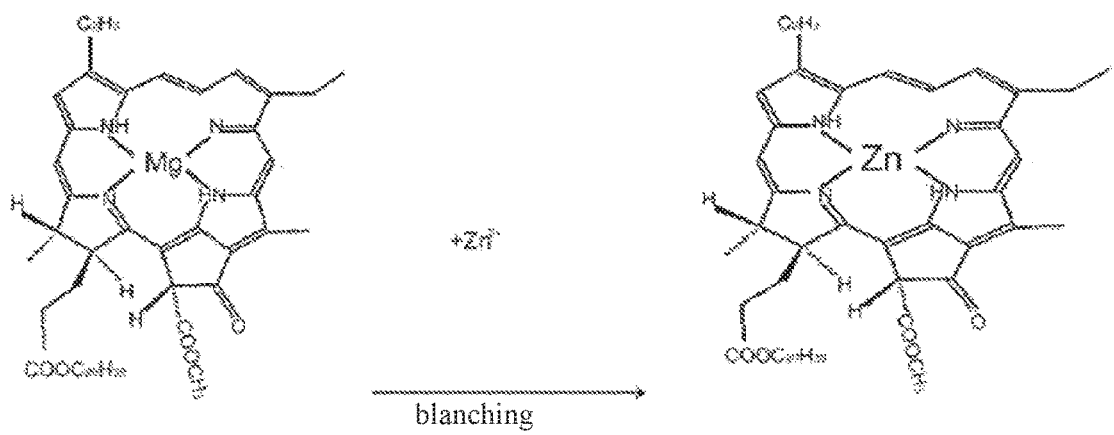
FIG. 1 shows a schematic diagram of the reaction process of blanching and color protection of the present invention.
Figure 2:
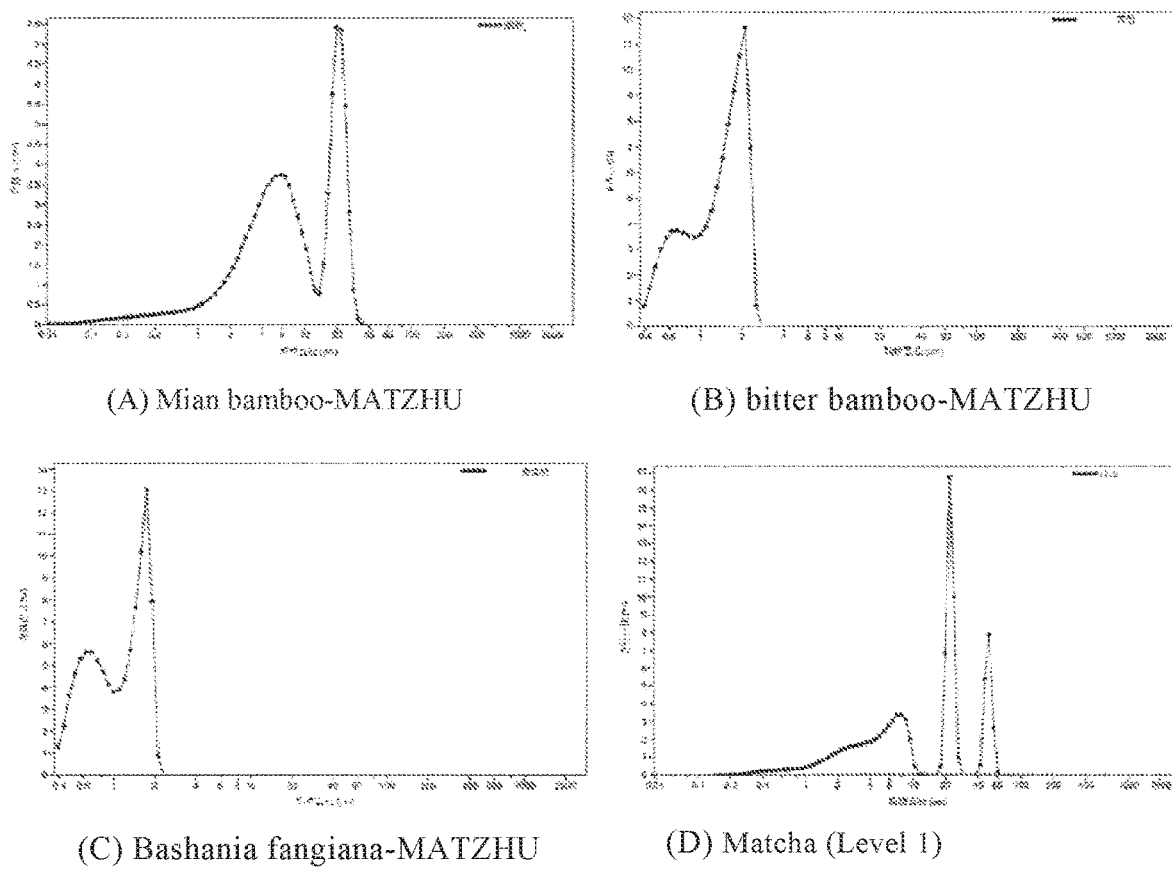
FIG. 2 shows a comparison of the particle sizes of the MATZHU prepared in Examples 1.3, 1.5 and 1.6 with that of the commercially available Grade 1 matcha (A) is for Mian bamboo-MATZHU. (B) is for bitter bamboo-MATZHU. (C) is for *Bashania fangiana*-MATZHU. And (D) is for Matcha (Grade 1).

Functional Comparison Between MATZHU and Matcha 2.1 Comparison of Powder Particle Size of MATZHU and Matcha Using LS-230 Coulter laser particle size analyzer, the powder particle size distribution of Mian bamboo-MATZHU, bitter bamboo-MATZHU and *Bashania fangiana*-MATZHU) were tested and compared with the control sample (commercially available Grade 1 matcha, provided by Zhejiang Tea Group Co., Ltd.), whose results are shown in FIG. 2 and Table 8.

TABLE 8

Comparison of powder particle size of MATZHU and matcha

| Related parameters | henon bamboo-MATZHU | Mian bamboo-MATZHU | bitter bamboo-MATZHU | Bashania fangiana-MATZHU | Matcha (first-class) |
|---|---|---|---|---|---|
| $D_{10}/\mu m$ | 1.85 | 1.72 | 0.58 | 0.53 | 1.98 |
| $D_{50}/\mu m$ (average particle size) | 16.86 | 6.98 | 1.46 | 1.15 | 19.20 |
| $D_{90}/\mu m$ | 40.73 | 22.54 | 2.17 | 1.82 | 48.38 |

FIG. 2 and Table 8 show that the particle sizes of the powder obtained by different bamboo species and different process parameters are significantly different. The average particle sizes of the four kinds of MATZHU samples are smaller than that of the compared commercially available Grade 1 matcha samples.

2.2 Comparison of the Contents of Conventional Ingredients in MATZHU and Matcha

Figure 3:
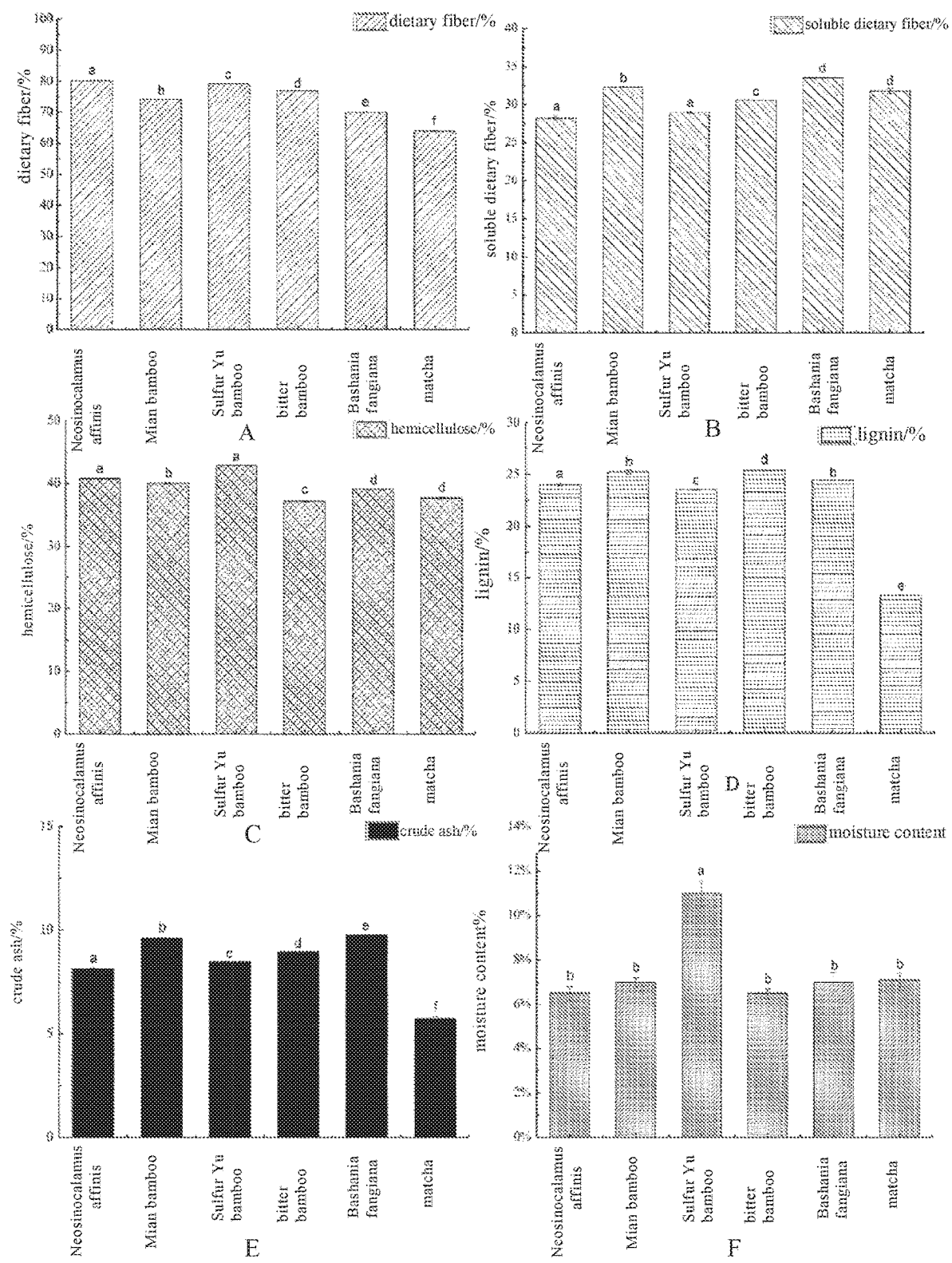
FIG. 3 shows a comparison of the contents of conventional ingredients of MATZHU prepared in Examples 1.2 to 1.6 with that of matcha. A is for dietary fiber. B is for soluble dietary fiber. C is for hemicellulose. D is for lignin. E is for crude ash. And F is for moisture content.

The contents of the conventional ingredients (including dietary fiber, soluble dietary fiber, hemicellulose, lignin, crude ash, and moisture) of the six MATZHU samples in Example 1 and the control sample (Grade 1 matcha) were measured. The contents of dietary fiber and soluble dietary fiber were determined according to the standard of GB 5009.88-2014. The content of lignin was determined according to the standard of GB/T 20805-2006. The moisture was determined according to the standard of GB/T 8304. And the total content of ash was determined according to the standard of GB/T 8306. The visual expression of the results is shown in FIG. 3, and the analysis is as follows.

Total dietary fiber: the dietary fiber contents of six kinds of MATZHU are between 63.0 and 80.2%, with an average of 76.1%. Among them, *Bashania fangiana*-MATZHU has the lowest content, and *Neosinocalamus affinis*-MATZHU has the highest content. At the same time, the measured dietary fiber content of matcha is 63.9%; and the total dietary fiber content of MATZHU is higher than matcha.

The above percentages are calculated on the dry basis of the sample.

According to the results, it can be known that the three chemical components which are the total dietary fiber content, lignin and crude ash, of the MATZHU are significantly higher than those of the matcha. The contents of soluble dietary fiber and hemicellulose of matcha is not much different from those of the MATZHU prepared in the above examples, and both fall within the range of the corresponding index of the MATZHU. The results is consistent with the fact that the degree of fiberization of bamboo leaves is higher than that of tea leaves.

2.3 Comparison of the Stability of MATZHU and Matcha

The light stability and thermal stability of two kinds of MATZHU (bitter bamboo-MATZHU and *Bashania fangiana*-MATZHU) and matcha were compared and analyzed.

2.3.1. Thermal Stability

The temperature was set at 180° C., which is a commonly used processing temperature for baking, and the time was 5, 15 and 30 minutes, respectively. The same amount of samples were laid flat in each petri dish and placed in an oven for heat treatment. The color difference analysis results are summarized in Table 9.

TABLE 9

Changes of color difference value of MATZHU and matcha after high temperature heating for different times

| Heat treatment intensity | color values | henon bamboo-MATZHU | bitter bamboo-MATZHU | *Bashania fangiana*-MATZHU | First-class matcha |
|---|---|---|---|---|---|
| 180° C. 0 min | L* | 55.93 ± 0.38$^a$ | 55.74 ± 0.48$^a$ | 56.47 ± 0.12$^a$ | 56.22 ± 0.28$^a$ |
|  | Δa | −12.14 ± 0.025$^a$ | −15.36 ± 0.036$^a$ | −13.28 ± 0.075$^b$ | −7.78 + 0.036$^c$ |
| 180° C. 5 min | L* | 50.33 ± 0.25$^a$ | 51.89 ± 0.45$^a$ | 51.77 ± 0.37$^a$ | 49.73 ± 0.29$^a$ |
|  | Δa | −7.65 ± 0.038$^a$ | −7.18 ± 0.045$^a$ | −8.32 ± 0.011$^a$ | −1.41 ± 0.015$^b$ |
| 180° C. 15 min | L* | 50.52 ± 0.37$^a$ | 51.72 ± 0.24$^a$ | 51.31 ± 0.57$^a$ | 40.67 ± 0.33$^b$ |
|  | Δa | −5.56 ± 0.033$^a$ | −6.70 ± 0.037$^a$ | −7.31 ± 0.028$^a$ | 3.36 ± 0.035$^b$ |
| 180° C. 30 min | L* | 43.32 ± 0.24$^a$ | 47.42 ± 0.28$^a$ | 49.02 ± 0.42$^b$ | 34.02 ± 0.42$^c$ |
|  | Δa | −5.31 ± 0.27$^a$ | −6.01 ± 0.03$^a$ | −6.59 ± 0.045$^a$ | 4.74 ± 0.033$^b$ |

Soluble dietary fiber: the soluble dietary fibers of six kinds of MATZHU samples are between 28.2 and 33.6%, with an average of 30.7%. Among them, *Bashania fangiana*-MATZHU has the highest content, and *Neosinocalamus affinis*-MATZHU has the lowest content. The content of the soluble dietary fiber of matcha is 31.8%, which falls within the variation range of the MATZHU sample.

Hemicellulose: the hemicellulose contents of six kinds of MATZHU samples are between 37.2 and 42.9%, wherein Sulfur Yu bamboo-MATZHU has the highest content, and bitter bamboo-MATZHU has the lowest content. The hemicellulose content of matcha is 37.7%, which falls within the variation range of the MATZHU sample.

Lignin: the lignin contents of six kinds of MATZHU samples are between 23.0 and 25.4%, with an average of 24.5%. Among them, bitter bamboo-MATZHU has the highest lignin content, and Sulfur Yu bamboo-MATZHU has the lowest content. The measured lignin content of the matcha is only 13.3%. The lignin content of the MATZHU is significantly higher than that of the matcha.

Crude ash: the crude ash contents of six kinds of MATZHU samples are between 8.1 and 11.9%, wherein *Bashania fangiana*-MATZHU has the highest content, and *Neosinocalamus affinis*-MATZHU has the lowest content. The crude ash content of matcha is only 5.7%, which is significantly lower than that of MATZHU.

It can be seen from Table 9 that before heating (180° C., 0 min), the brightness values of MATZHU and matcha were close, but the greenness of MATZHU was greater than that of matcha. After treatment at 180° C. for 5 min, the brightness of both MATZHU and Matcha decreased, and the greenness decreased. After heated at 180° C. for 15 min, the Δa value of matcha changed from negative values to positive values, indicating that its hue changed from green to red, that is, the color changed from yellow-green to tan. Meanwhile, the Δa values of three MATZHU samples were still negative values (−5.56 for henon bamboo-MATZHU, −6.70 for bitter bamboo-MATZHU, −7.31 for *Bashania fangiana*-MATZHU), which were not significantly different from the values after heated at 180° C. for 5 minutes. After heated at 180° C. for 30 minutes, the MATZHU still had an acceptable green color, while the matcha had completely browned.

According to this result, it can be known that MATZHU has better light stability than matcha. It can be baked at 180° C. for 30 minutes without turning brown, and the green color of MATZHU at this time was close to the green color at the beginning of the Grade 1 matcha. The matcha changed from green to reddish brown after being baked at 180° C. for 15 minutes.

2.3.2 Light Stability

Ultraviolet (UV) radiation was used to observe the destructive effect on the color of the sample. Three samples were simultaneously irradiated with 10 8 w UV lamps, and the samples were placed 30 cm below the lamps. Color difference analysis was performed after 60, 120, and 180 minutes of irradiation, respectively. The changes in color value are shown in Table 10.

After UV irradiation of MATZHU and matcha, the change degree of L* and Δa values were different. After being irradiated with ultraviolet light for the same period of time, the greenness of matcha was more damaged than that of MATZHU, and it appeared a little brown. The data in Table 12 shows that after 60 minutes of UV irradiation, the brightness value reduction of the MATZHU was greater than that of the matcha, but the greenness value reduction of the matcha was greater than that of the MATZHU. After the matcha was irradiated for 180 min, the Δa value was close to 0, indicating that its color was about to change from green to red and began to turn brown. At this time, the Δa values of the two MATZHU samples still remained negative. It shows that compared with matcha, MATZHU has better light stability.

TABLE 10

Changes of color value of MATZHU and matcha under different UV irradiation intensity

| UV exposure time | color values | bitter bamboo-MATZHU | *Bashania fangiana*-MATZHU | first-class matcha |
|---|---|---|---|---|
| UV 0 min | L* | 55.74 ± 0.48$^a$ | 56.47 ± 0.12$^a$ | 56.22 ± 0.28$^a$ |
| | Δa | −15.36 ± 0.036$^a$ | −13.28 ± 0.075$^b$ | −7.78 + 0.036$^c$ |
| UV 60 min | L* | 38.48 ± 0.89$^a$ | 36.54 ± 0.54$^b$ | 40.15 ± 1.03$^c$ |
| | Δa | −10.76 ± 0.025$^a$ | −8.37 ± 0.015$^b$ | −4.48 ± 0.012$^c$ |
| UV 120 min | L* | 32.44 ± 1.13$^a$ | 38.33 ± 1.55$^b$ | 36.09 ± 2.10$^c$ |
| | Δa | −8.45 ± 0.022$^a$ | −6.69 ± 0.014$^b$ | −2.97 ± 0.004$^c$ |
| UV 180 min | L* | 24.05 ± 0.82$^a$ | 23.09 ± 1.73$^a$ | 30.69 ± 2.24$^c$ |
| | Δa | −5.35 ± 0.01$^a$ | −3.66 ± 0.014$^b$ | −0.58 ± 0.008$^c$ |

2.4 Sensory Qualities of MATZHU and Matcha

Take two MATZHU samples (bitter bamboo-MATZHU and *Bashania fangiana*-MATZHU) and the commercially available Grade 1 matcha control products for sensory quality evaluation test.

With reference to the relevant literature on ultrafine green tea powder and the tea powder standard issued by the Ministry of Agriculture, 15 sensory assessors were selected to conduct sensory evaluation in the four aspects of the shape, powder aroma, taste and soup color of 2 MATZHU and 1 matcha samples (see Table 11 for indicator settings).

Figure 4:
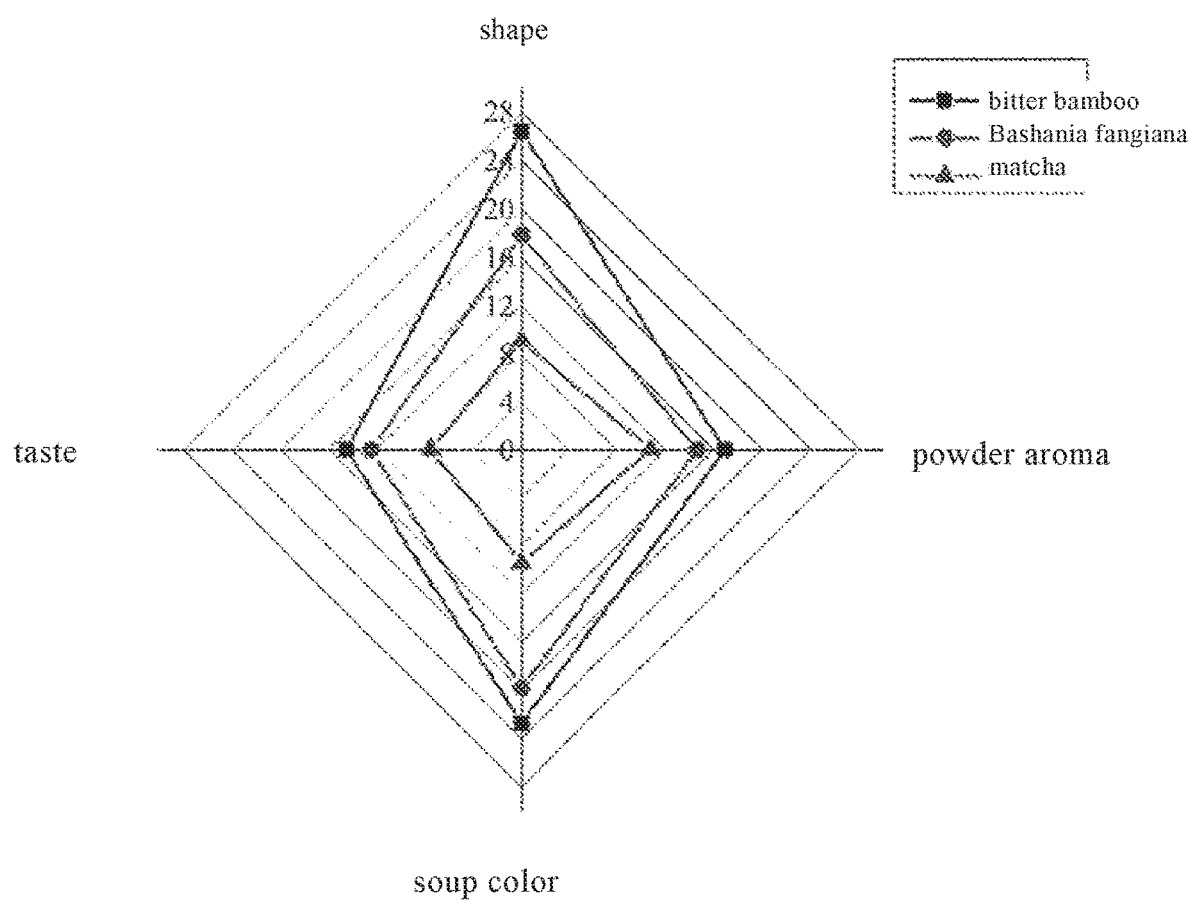
FIG. 4 shows the sensory evaluation results of the matcha and MATZHU prepared in Examples 1.5 and b 1.6.

The sensory evaluators performed statistical analysis on the scoring results (average±standard error) of the three samples. The results are shown in FIG. 4. The highest scores of the two samples were bitter bamboo-MATZHU, followed by *Bashania fangiana*-MATZHU, and matcha had the lowest score. Judging from the scores of the four indicators, MATZHU was significantly higher than Matcha in appearance and brewing soup color, and scores were similar in taste and powder aroma. MATZHU has a greener color than matcha, so it was loved by the evaluators. After the matcha was brewed in boiling water, the chlorophyll was decomposed by heat, and the tea soup quickly appeared yellow-brown, so the score is lower than that of the MATZHU; while the greenness of the MATZHU was more stable, and the soup color can remain green for a long time after brewing.

TABLE 11

Sensory evaluation table
Sample serial number:
Evaluators serial number:

| Item | Score grade | Quality characteristics | Score |
|---|---|---|---|
| shape 30 points | 30-21 points | emerald and shiny, uniform color | |
| | 20-11 points | light green, not obvious gloss, uniform color | |
| | 10 points and below | yellow-green or black-green, dull, uneven color | |
| powder aroma 20 points | 20-15 points | fresh fragrance, with bamboo fragrance, no special smell | |
| | 14-10 points | lighter bamboo fragrance, no special smell | |
| | 9 points and below | almost no bamboo fragrance, special smell | |
| brewing taste 20 points | 30-21 points | delicate mouthfeel and refreshing taste | |
| | 20-11 points | a bit rough mouthfeel and very light taste | |
| | 10 points and below | rough mouthfeel and green taste | |
| brewing soup color 30 points | 20-15 points | dark green soup, shiny | |
| | 14-10 points | light green soup, a little shiny | |
| | 9 points and below | yellow-green soup, dull, turbid | |

EXAMPLE 3

Comparison of Biological Health Effects of MATZHU and Matcha

Metabolic syndrome (MS) refers to a clinical syndrome which takes a group of disease risk factors such as centripetal obesity, type 2 diabetes or impaired glucose tolerance, hypertension, abnormal lipid metabolism and insulin resistance (IR) as pathophysiological basis. In recent years, metabolic syndrome has shown a high incidence and a tendency toward youth, and its prominent characteristics are obesity, insulin resistance and abnormal glucose tolerance. In addition to being rich in fibrous components, MATZHU also contains a variety of bamboo-specific biologically active substances, and has strong anti-free radical and anti-oxidant activities, and can also play a role in anti-inflammatory, lipid-lowering and cardio-cerebrovascular protection. Matcha is also rich in biologically active ingredients (such as tea polyphenols, tea polysaccharides, theanine, etc.), and many studies have proved that it can effectively prevent obesity and stroke, and reduce the risk of cerebral thrombosis and hyperlipidemia.

The present invention uses two kinds of MATZHU (bitter bamboo-MATZHU and *Bashania fangiana*-MATZHU) as representatives, and uses a commercially available Grade 1 matcha as a reference, and adopts the mice model with metabolic syndrome to conduct a comparative test study.

3.1 Materials and Methods 3.1.1 Test Dose Configuration

MATZHU and matcha were added to mice's high-fat feed in a certain proportion. The four test groups were as follows: the first group was 2.5% bitter bamboo-MATZHU+high-fat feed, the second group was 5.0% bitter bamboo-MATZHU+high-fat feed, and the third group was 2.5% *Bashania fangiana*-MATZHU+high-fat feed, and the fourth group was 2.5% matcha+high-fat feed.

3.1.2 Grouping of Test Animals

Sixty six-week-old C57BL/6J male mice were adaptively fed with basic feed for 5 days, and those with no adverse reactions, that is, normal eating, drinking and activities, were included in the experiment. The mice were randomly divided into 6 groups to ensure that the average body weight of each group was close, and were fed respectively with the following feeds: basic feed, high-fat feed, bitter bamboo-MATZHU with low dose, bitter bamboo-MATZHU with high dose, *Bashania fangiana*-MATZHU with low dose group and matcha with low dose. During the test period, every 5 mice were in a cage, under the feeding environment of a light period of 12 h, a temperature of 23±2° C. and a relative humidity of 50-70%, and they could freely eat and drink water for 12 weeks. The experimental grouping of mice is shown in Table 12.

TABLE 12

Grouping of experimental mice

| Serial number | Group | Quantity (n) | Group code |
|---|---|---|---|
| 1 | Basic feed control group | 10 | Bas-C |
| 2 | High-fat feed control group | 10 | HFD |
| 3 | High-fat feed + 2.5% bitter bamboo-MATZHU | 10 | 2.5% BP1-HFD |
| 4 | High-fat feed + 5.0% bitter bamboo-MATZHU | 10 | 5.0% BP1-HFD |
| 5 | High-fat feed + 2.5% *Bashania fangiana*-MATZHU | 10 | 2.5% BP2-HFD |
| 6 | High fat feed + 2.5% matcha | 10 | 2.5% M-HFD |

Note:
BP1 is the bitter bamboo-MATZHU made in Example 1.5; BP2 is the *Bashania fangiana*-MATZHU made in Example 1.6

3.1.3 Records of Changes in the Weight of Mice and the Weight of Various Organs

During the feeding period, the general condition, changes in diet, changes in actions (autonomous activity, mental state) and changes in hair of the mice were observed every day. The mice were weighed once a week and the weight changes were recorded. After 12 weeks of feeding, the liver, kidney and spleen of the mice were carefully removed and weighed, and the coefficient of viscera-body ratios were calculated. Simultaneously, epididymal fat and peri-renal fat were removed and weighed. All organs were then stored at −80° C.

3.1.4 Blood Sample Collection and Analysis of Routine Blood Biochemical Indicators After 12 weeks of feeding, the mice were euthanized in a $CO_2$ feeding box, and then blood was quickly drawn from the heart, centrifuged to take serum (3500 r/min, 15 min), for detection of triglyceride (TG), total cholesterol (TC), low density lipoprotein cholesterol (LDL-c), high density lipoprotein cholesterol (HDL-c), free fatty acid (FFA) and other indicators.

3.1.5 Fasting Blood Glucose (FBG) and Fasting Insulin (FINS) Level Test

After feeding for 12 weeks, the mice were treated for fasting for 12 hours (without water deprivation) respectively, and then blood was drawn to detect the fasting blood glucose (FBG) value of the mice using a Roche blood glucose meter and to determine fasting insulin (FINS) content of the mice by ELISA kit.

3.1.6 Insulin Tolerance (ITT) Test

After feeding for 12 weeks, and after fasting for another 6 hours (without water deprivation), blood was collected from the tail to determine the blood glucose value, which was taken as the blood glucose value at time zero (0 min) of the insulin resistance experiment. Immediately afterwards, 0.75 U/Kg·BW insulin physiological saline solution (concentration: 0.075 U/mL) was injected intraperitoneally into the mice. Then the blood glucose levels of the mice within 30, 60, 90 and 120 minutes after injection were tested and record. After the test, the mice were resumed feeding.

3.1.7 Glucose Tolerance (GTT) Test

After feeding for 12 weeks, and after fasting for another 6 hours (without water deprivation), blood was collected from the tail to measure the blood glucose value, and this value was used as the blood glucose value at the zero time (0 min) of the glucose tolerance test. Immediately, a physiological saline solution of glucose (concentration: 0.15 g/mL) was injected into the abdominal cavity of the mouse at a dosage of 1.5 g/kg·BW, and the blood glucose levels of the mouse were measured at 30, 60, 90, and 120 min after the injection. After the test, the mice were resumed feeding.

3.1.8 Liver Oxidative Stress Index Test

At the end of the test, the mice were euthanized and the livers were quickly removed. The blood was washed away as much as possible, weighed, and a small portion was added with 4° C. physiological saline and high-speed homogenate to make a 10% homogenate. Take the supernatant by centrifugation at 3000 r/min for 20 min. Then, the SOD, GSH-Px activity and MDA level in liver homogenate were determined using the kit produced by Nanjing Jiancheng Bioengineering Research Institute.

3.1.9 Serum Inflammatory Factors Detection

Elisa kit was used to detect serum interleukin-6 (IL-6), tumor necrosis factor-α (TNF-α) and chemokine (MCP-1).

3.1.10 Serum Cytokine Detection

Enzyme-linked immuno assay was used to detect leptin, adiponectin (ADPN), and lipopolysaccharide (LPS) in the serum of mice. The detection method was carried out according to the Elisa kit method.

3.1.11 Intestinal Flora Detection

The 12-week-end mouse colonic stools were taken for high-throughput sequencing, using Illumina PE250 sequencing, DNA of intestinal microorganisms was extracted from the stools, and then PCR amplified, and finally, the categories of intestinal microorganisms were identified by sequencing.

3.2 Test Results 3.2.1 Efficacy of MATZHU and Matcha for Weight Loss and Fat Loss The weight loss and fat loss effects of MATZHU and Matcha were evaluated by weight gain of mice, various organ indexes and blood biochemical indicators.

3.2.1.1 Effects on the Body Weight of Experimental Mice

Figure 5:
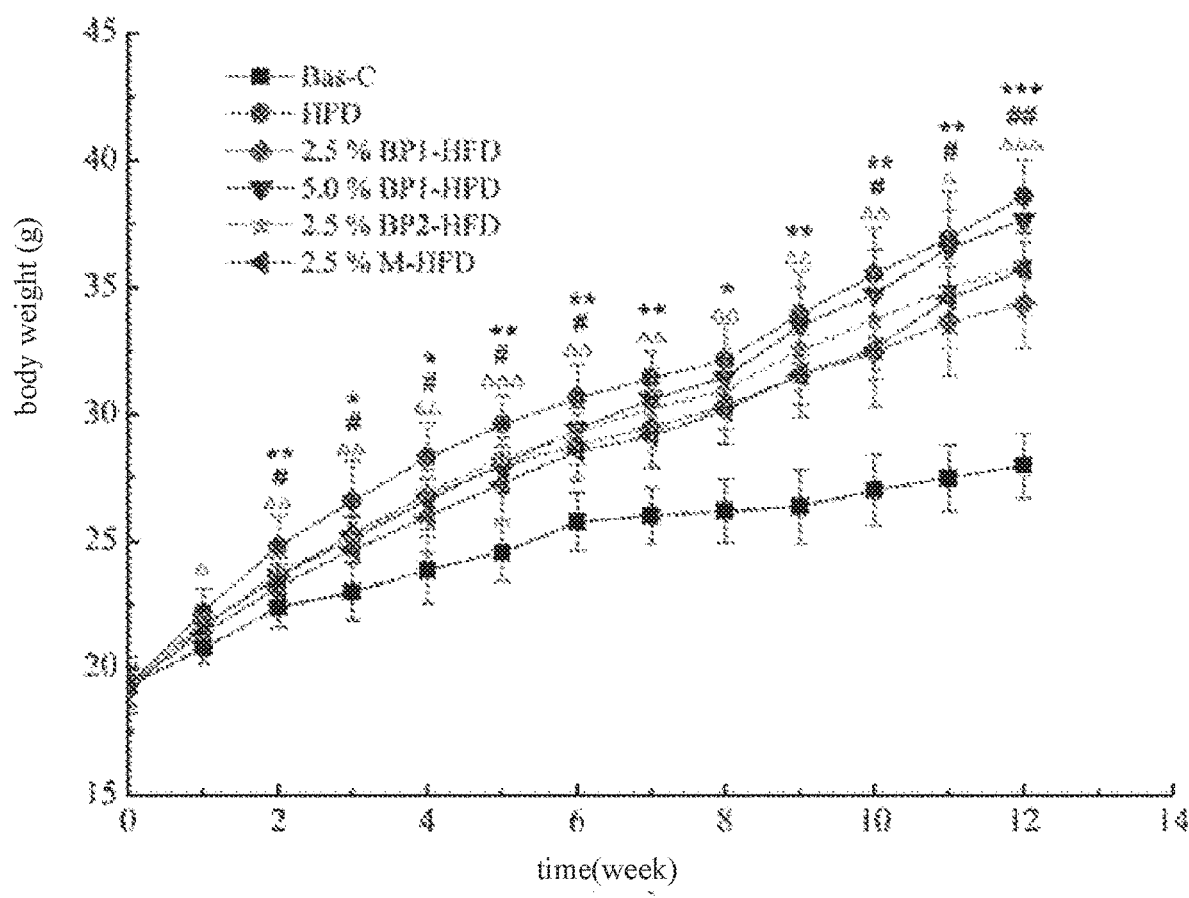
FIG. 5 shows a graph of weight gain in mice with metabolic syndrome.

The mice in the high-fat feed model group showed obesity characteristics, and the weight gain of the mice in the basic feed group was significantly lower than that in the high-fat feed group. The effect of the feed fortified by MATZHU and matcha on body weight is shown in FIG. 5.

Among the 4 test groups, the third group (high-fat feed+ 2.5% bitter bamboo-MATZHU) showed the best effect on the control of mouse body weight. After 12 weeks, the average body weight of this group of mice was significantly lower than that of the high-fat group. However, the effect on weight control was not obvious when the amount of bitter bamboo-MATZHU increased to 5% (the fourth group). The control effect on the body weight of mice of the sixth group (high-fat feed+2.5% matcha) was only after that of the same dose of bitter bamboo-MATZHU, and the average body weight at the end of the experiment was also significantly lower than that of the high-fat group. The weight-loss effect of the fifth group (high-fat feed+2.5% *Bashania fangiana*-MATZHU) was between those of the same dose of bitter bamboo-MATZHU (third group) and matcha (sixth group).

3.2.1.2 Effects on the Organ Index of Experimental Mice

Figure 6:
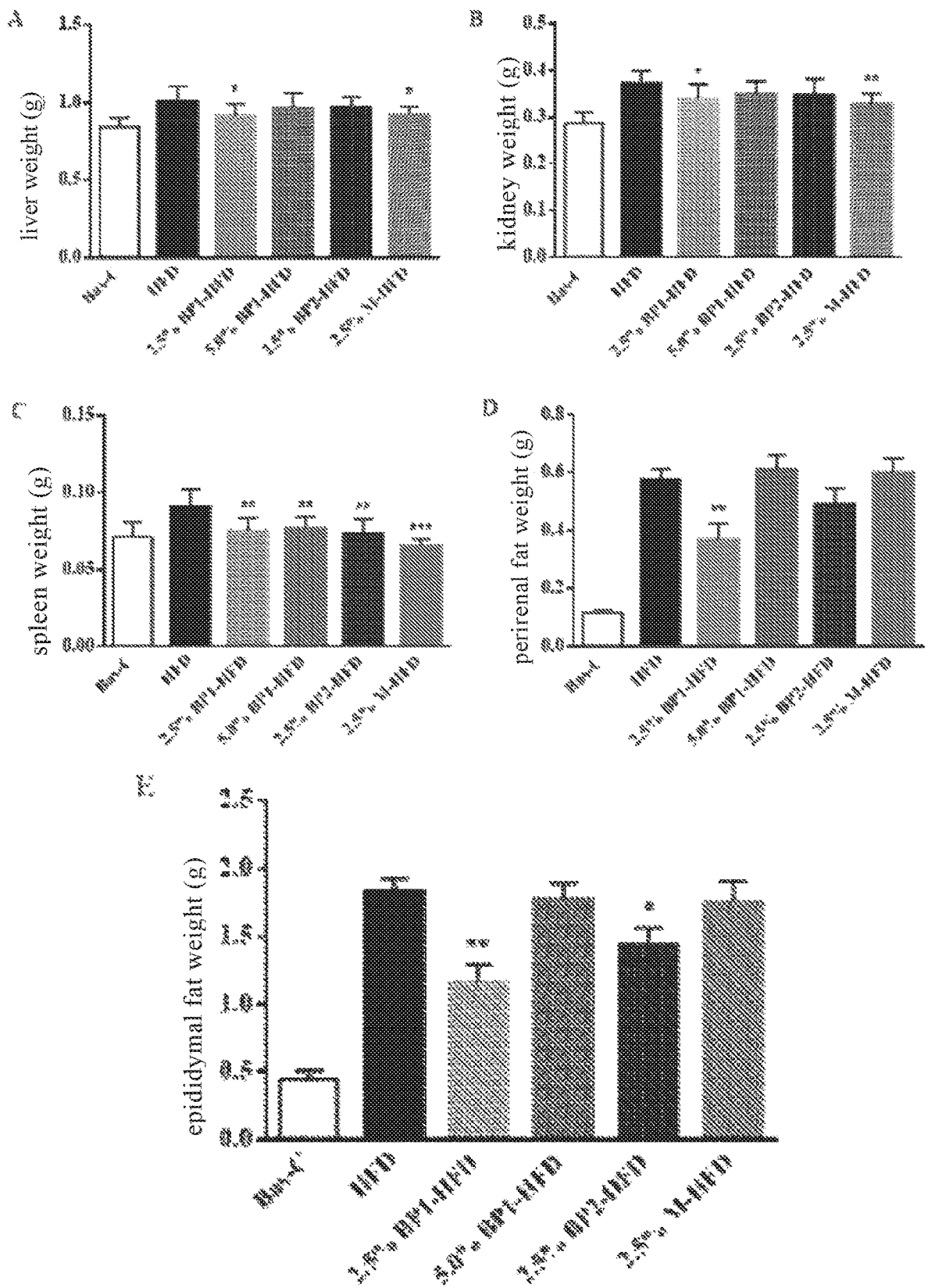
FIG. 6 shows a bar chart of the weights of some organs and tissues in the 12th week of the experimental mice with metabolic syndrome. A is for liver. B is for kidney. C is for spleen. D is for perirenal fat. E is for epididymal fat.

At the end of the experiment, some tissues and organs of 6 groups of mice were taken, including liver, kidney, spleen, peri-renal fat and epididymal fat, and then these organs were weighed separately. The results are shown in FIG. 6.

In terms of liver and kidney weights, only the 2.5% bitter bamboo-MATZHU and 2.5% Matcha groups showed significant weight-reducing effects on organs, and the liver and kidney weights of the remaining test groups were not significantly different from those in the high-fat group. For the spleen, the weight of the spleen of the mice added with MATZHU and matcha was significantly lower than that of the high-fat group. Wherein, the spleen weight of the 2.5% matcha group was significantly different from that of the high-fat group. Perirenal fat and epididymal fat are the two fat tissues in mice that have the highest mass and are most closely related to obesity. The mice in the 2.5% bitter bamboo-MATZHU group had significantly lower perianal fat than the high-fat group, which was significantly better than the other three test group. Both 2.5% bitter bamboo-MATZHU and 2.5% *Bashania fangiana*-MATZHU had the effect on reducing epididymal fat. Wherein, bitter bamboo had better effect, reducing the epididymal fat of mice by nearly half.

3.2.1.3 Effects on Blood Lipid Levels in Experimental Mice

At the end of feeding, the serum of mice was taken to test the blood biochemical indicators, including triglyceride (TG), total cholesterol (TC), low density lipoprotein cholesterol (LDL-c), high density lipoprotein cholesterol (HDL-c) and free fatty acids (FFA). The results are shown in Table 13.

TABLE 13

Effects of 12 week dietary interventions of MATZHU and matcha on blood lipid levels in mice (mmol/L, $\bar{x} \pm s$, n = 10)

| | | | group | | | |
|---|---|---|---|---|---|---|
| indicators | 1 normal feed | 2 high-fat feed | 3 high fat feed + 2.5% bitter bamboo | 4 high fat feed + 5.0% bitter bamboo | 5 high fat feed + 2.5% Bashania fangiana | 6 high fat feed + 2.5% matcha |
| TG | 1.11 ± 0.17 $^a$ | 1.30 ± 0.16 $^b$ | 1.25 ± 0.16 $^b$ | 1.35 ± 0.16 $^b$ | 1.32 ± 0.17 $^b$ | 1.17 ± 0.1 $^a$ |
| TC | 3.06 ± 0.33 $^a$ | 3.99 ± 0.32 $^b$ | 3.67 ± 0.30 $^c$ | 4.22 ± 0.34 $^b$ | 4.21 ± 0.31 $^b$ | 4.49 ± 0.33 $^d$ |
| LDL-c | 0.31 ± 0.04 $^a$ | 0.40 ± 0.04 $^b$ | 0.36 ± 0.04 $^c$ | 0.40 ± 0.03 $^b$ | 0.38 ± 0.06 $^b$ | 0.42 ± 0.05 $^b$ |
| HDL-c | 2.80 ± 0.20 $^a$ | 2.48 ± 0.13 $^b$ | 2.73 ± 0.18 $^a$ | 2.58 ± 0.2 $^b$ | 2.65 ± 0.15 $^{ab}$ | 2.67 ± 0.19 $^a$ |
| FFA | 2.11 ± 0.16 $^a$ | 2.36 ± 01.9 $^b$ | 1.97 ± 0.23 $^a$ | 2.01 ± 0.16 $^a$ | 1.97 ± 0.11 $^a$ | 1.63 ± 0.13 $^c$ |

A high-fat diet leads to obesity in mice. The accumulation of fat in obese mice increased, and it also caused an increase in the levels of TG, TC, LDL-c and FFA in their blood, and reduced HDL-c levels to some extent. It can be seen from Table 13 that matcha has the best TG-reducing effect. After 3 months of dietary fortification with a 2.5% dose, the TG level of high-fat mice is close to that of the normal feed group. The TG-reducing effect of MATZHU is not obvious. The group strengthened by the 2.5% bitter bamboo-MATZHU showed the most significant reducing effect on TC, while 5.0% bitter bamboo-MATZHU and 2.5% *Bashania fangiana*-MATZHU showed no effect on TC, but TC of the 2.5% matcha group is significantly higher than that of high-fat model group.

For LDL-c levels, only the 2.5% bitter bamboo-MATZHU group showed a significant decrease, and the remaining three test groups had no significant difference when compared with the high-fat group. For HDL-c, 2.5% bitter bamboo-MATZHU group exhibits significant improvement effect, followed by 2.5% matcha, and then 2.5% *Bashania fangiana*-MATZHU.

Due to the imbalance of glucose and lipid metabolism, free fatty acids (FFA) in obese mice will increase significantly. The data in Table 13 shows that in all test groups, the increase in FFA levels were inhibited, wherein 2.5% matcha group showed the best effect, followed by 2.5% bitter bamboo and *Bashania fangiana*, and the last was 5.0% bitter bamboo-MATZHU. It once again proved that the 2.5% dosage is a reasonable level. Based on the above indicators, in the 4 test groups, 2.5% bitter bamboo-MATZHU group showed the best fat-lowering effect, followed by 2.5% matcha.

3.2.2 The Improvement of MATZHU and Matcha on Insulin Resistance in Mice

The test results of fasting blood glucose (FBG) and fasting insulin (FINS) of mice at the end of the 12-week test are shown in Table 14.

TABLE 14

Effects of 12-week dietary interventions of MATZHU and Matcha on fasting blood glucose and fasting insulin in mice ($\bar{x} \pm s$, n = 10)

| group | FBG (mmol/L) | FINS (mU/L) | HOME-IR |
|---|---|---|---|
| normal feed | 3.81 ± 0.56 $^a$ | 5.28 ± 0.72 $^a$ | 0.94 ± 0.19 $^a$ |
| high-fat feed | 6.89 ± 0.70 $^b$ | 6.48 ± 0.76 $^b$ | 1.99 ± 0.39 $^b$ |
| High-fat feed + 2.5% bitter bamboo-MATZHU | 5.88 ± 0.90 $^c$ | 5.31 ± 0.62 $^a$ | 1.39 ± 0.30 $^c$ |

TABLE 14-continued

Effects of 12-week dietary interventions of MATZHU and Matcha on fasting blood glucose and fasting insulin in mice ($\bar{x} \pm s$, n = 10)

| group | FBG (mmol/L) | FINS (mU/L) | HOME-IR |
|---|---|---|---|
| High-fat feed + 5.0% bitter bamboo-MATZHU | 6.08 ± 0.83 $^{bc}$ | 6.21 ± 0.74 $^b$ | 1.68 ± 0.35 $^{bc}$ |
| High-fat feed + 2.5% *Bashania fangiana*-MATZHU | 5.84 ± 0.87 $^c$ | 5.44 ± 0.67 $^a$ | 1.41 ± 0.30 $^c$ |
| High fat feed + 2.5% matcha | 6.93 ± 0.96 $^b$ | 6.01 ± 0.66 $^{ab}$ | 1.87 ± 0.42 $^b$ |

It can be seen from Table 14 that a high-fat diet can cause an increase in fasting blood glucose (FBG) and fasting insulin (FINS) in mice. HOME-IR is the insulin resistance index. The larger the value is, the lower the insulin sensitivity is, and the more obvious the insulin resistance symptoms are. Both 2.5% bitter bamboo-MATZHU and 2.5% Bashania fangiana-MATZHU can better improve the insulin resistance brought by high-fat diet and reduce the fasting insulin level in mice. The 5.0% bitter bamboo-MATZHU and matcha group showed no significant improvement effect.

Figure 7:
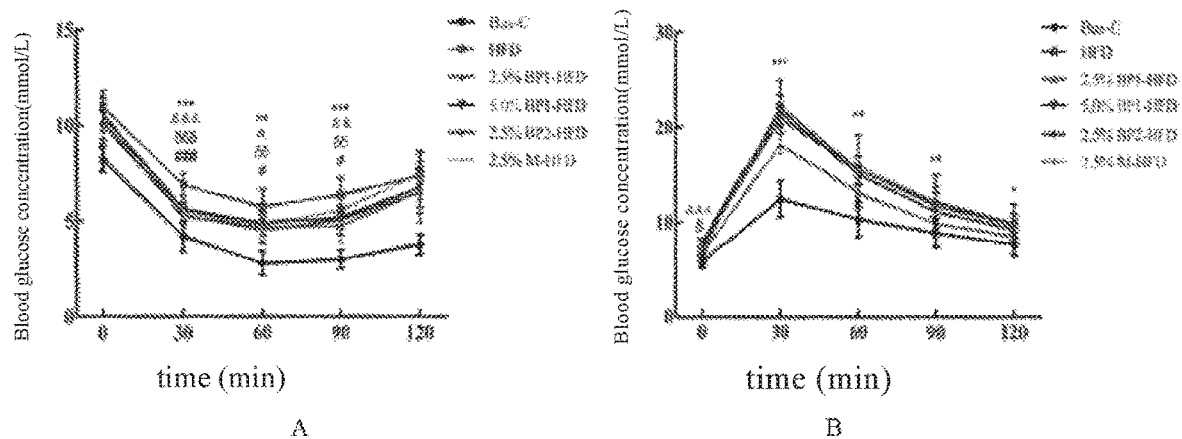
FIG. 7 shows the change of insulin sensitivity in the 12th week of the experimental mice with metabolic syndrome. A is for the insulin tolerance test (ITT). B is for the glucose tolerance test (GTT).

FIG. 7 shows the changes in insulin sensitivity of mice at the end of the test, wherein A is for the insulin tolerance test (ITT), and B is for the glucose tolerance test (GTT). In the insulin tolerance test (ITT), the mice in the high-fat group were affected by the high-fat diet and their insulin sensitivity was reduced. After insulin was injected, insulin could not act quickly to promote the decomposition and utilization of glucose in the blood. The mice in the test group added with MATZHU and matcha had improved insulin sensitivity, but after injected with insulin, it promoted the rapid action and promoted the decomposition and utilization of glucose in the blood In the glucose tolerance test (GTT), after injecting glucose solution into mice, the glucose level in the blood temporarily increased. With the action of factors such as insulin, glucose was slowly decomposed and utilized, thereby restoring the initial value High-fat mice, due to insulin resistance, cannot decompose glucose as quickly as normal mice, so the glucose content in the blood increased sharply and decreased slowly. The test group added with 2.5% bitter bamboo-MATZHU showed significant improvement of this symptom, making its blood glucose value close to that of normal group mice.

3.2.3 MATZHU and Matcha Reduced the Oxidative Stress Response in the Liver of Experimental Mice Table 15 shows the effects of the 12-week dietary intervention of MATZHU and Matcha on the evaluation indexes of oxidative stress in the liver of mice.

TABLE 15

Effects of 12-week dietary intervention of MATZHU and matcha on liver oxidative stress evaluation indexes in mice ($\bar{x} \pm s$, n = 10)

| group | SOD (U/mg protein) | GSH-Px (U/mg protein) | MDA (nmol/mg protein) |
|---|---|---|---|
| normal feed | 78.88 ± 3.99 $^a$ | 318.85 ± 19.83 $^a$ | 0.34 ± 0.02 $^a$ |
| high-fat feed | 84.32 ± 2.37 $^b$ | 387.25 ± 13.84 $^b$ | 0.38 ± 0.03 $^b$ |
| high-fat feed + 2.5% bitter bamboo-MATZHU | 77.53 ± 5.38 $^a$ | 377.22 ± 13.54 $^b$ | 0.32 ± 0.03 $^a$ |
| high-fat feed + 5.0% bitter bamboo-MATZHU | 84.06 ± 4.53 $^b$ | 415.33 ± 16.95 $^c$ | 0.31 ± 0.04 $^a$ |
| high-fat feed + 2.5% Bashania fangiana-MATZHU | 78.91 ± 5.65 $^a$ | 379.79 ± 16.52 $^b$ | 0.34 ± 0.04 $^a$ |
| high fat feed + 2.5% matcha | 92.38 ± 5.22 $^c$ | 462.94 ± 17.18 $^d$ | 0.35 ± 0.03 $^{a\,b}$ |

SOD and GSH-Px in the liver are the main antioxidant enzymes in the body and have a strong ability to scavenge free radicals. The data in Table 15 shows that the SOD levels of the mice in the high-fat group, 5.0% bitter bamboo-MATZHU and 2.5% matcha group were significantly higher than those of the normal group, while the SOD activity of the mice in the 2.5% bitter bamboo-MATZHU and Bashania fangiana-MATZHU groups are comparable to that of the normal group. In terms of GSH-Px levels, 2.5% bitter bamboo-MATZHU and Bashania fangiana-MATZHU had the level between that of the normal group and the high-fat group, while the 5.0% bitter bamboo-MATZHU and 2.5% matcha group had the levels significantly higher than the high-fat group. From the perspective of reducing the level of lipid peroxide products, the effect of MATZHU is generally better than that of matcha, and bitter bamboo is preferable.

Oxidative stress is the generation of an excess of reactive oxygen radicals (ROS) in the body after being stimulated by various harmful factors. ROS is an important cause of insulin resistance. A long-term high-fat and high-sugar diet will cause the body to produce a large amount of ROS. Studies have shown that in order to resist the large amount of ROS production, the body's antioxidant enzymes will also be compensated accordingly to counteract the damage of free radicals to the body. However, as the degree of oxidative stress continues to increase, the increased compensatory activity of antioxidant enzymes will be unable to prevent free radical damage, which will eventually lead to decreased enzyme activity and increased oxidative damage to the body. According to the data in Table 15, the high-fat diet increased the degree of oxidative stress in mice. The dietary intervention of MATZHU can effectively reduce the oxidative stress in the body, and a 2.5% MATZHU addition is preferred.

Figure 8:
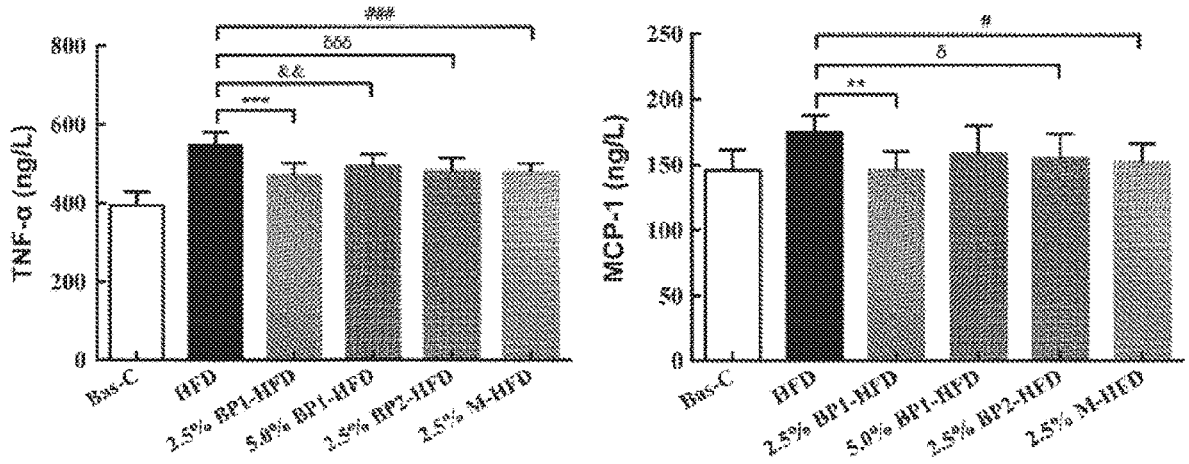
FIG. 8 shows the levels of inflammatory factors in the serum of the experimental mice with metabolic syndrome. The left is the TNF-α content chart, and the right is the MCP-1 content chart.

3.2.4 Effect of MATZHU and Matcha on Serum Inflammatory Factor Levels in Experimental Mice The effect of 12-week dietary intervention of MATZHU and Matcha on the expression of serum inflammatory factors in obese mice is shown in FIG. 8.

Many studies have proved that obesity is closely related to type 2 diabetes and inflammation, and other studies have shown that obesity is due to the body's long-term low inflammation infiltration state, that is, chronic inflammation. MCP-1 is a chemokine. The enlarged adipose tissue in obese people will release a large amount of MCP-1, thereby inducing a large number of phagocytes into the adipose tissue and releasing a large number of inflammatory factors. Among them, IL-6 and TNF-α are two proinflammatory factors closely related to obesity. When the levels of them increase, it indicates that the body has increased inflammation infiltration degree.

As can be seen from FIG. 8, the levels of TNF-α and MCP-1 in mice in the high-fat group were significantly higher than those of the normal group, indicating that the obese mice in the high-fat group had inflammation. The high-fat mice added with bitter bamboo-MATZHU, Bashania fangiana-MATZHU and matcha had significantly lower TNF-α content, indicating that different doses of MATZHU and matcha could significantly inhibit the secretion of proinflammatory factors (TNF-α) caused by obesity The 2.5% added amount of bitter bamboo-MATZHU, Bashania fangiana-MATZHU and matcha can significantly reduce the content of MCP-1, but the high dose (5.0% bitter bamboo-MATZHU) did not significantly reduce the content. The test results show that dietary intervention with appropriate doses of MATZHU and matcha can significantly improve the inflammation infiltration in obese mice.

3.2.5 Effect of MATZHU and Matcha on Cytokine Levels in Experimental Mice

Table 16 shows the effect of 12-week dietary intervention of MATZHU and Matcha on serum cytokine levels in obese mice.

TABLE 16

Effect of 12-week dietary interventions of MATZHU and Matcha on the expression of serum inflammatory factors in obese mice ($\bar{x} \pm s$, n = 10)

| group | LEP (pg/mL) | ADP (pg/mL) | LPS (U/mL) |
|---|---|---|---|
| normal feed | 158.40 ± 34.94 [a] | 86.49 ± 12.98 [a] | 1.86 ± 0.29 [a] |
| high-fat feed | 209.11 ± 36.20 [b] | 67.75 ± 12.69 [b] | 2.16 ± 0.25 [b] |
| high-fat feed + 2.5% bitter bamboo-MATZHU | 171.36 ± 36.69 [a] | 81.33 ± 12.80 [a] | 1.56 ± 0.30 [c] |
| high-fat feed + 5.0% bitter bamboo-MATZHU | 199.40 ± 33.31 [b] | 76.08 ± 11.40 [a b] | 1.80 ± 0.12 [a] |
| high-fat feed + 2.5% *Bashania fangiana*-MATZHU | 191.89 ± 37.00 [a b] | 79.49 ± 11.82 [a b] | 1.76 ± 0.31 [a] |
| high fat feed + 2.5% matcha | 178.80 ± 37.50 [a b] | 80.54 ± 11.84 [a] | 1.68 ± 0.25 [a] |

Leptin (LEP) is a circulating hormone secreted by fat cells, which mainly acts on the central nervous system. It can reduce appetite and energy intake by inhibiting the synthesis of neuropeptide Y, thereby achieving the effect of weight loss and fat reduction. Studies have shown that too high or too low leptin may cause insulin resistance (IR). The data in Table 16 shows that the serum leptin levels of mice in the high-fat group were significantly higher than those of the normal group, indicating that the high-fat diet caused mice to have leptin resistance. The 2.5% added bitter bamboo-MATZHU showed the best effect on reducing serum leptin levels in mice, followed by 2.5% matcha, then 2.5% *Bashania fangiana*-MATZHU, and the effect of 5% added bitter bamboo-MATZHU was not significant.

Adiponectin (ADP) is closely related to obesity and glucose and fat metabolism. Studies have shown that the level of ADP in obese people is significantly reduced. It is believed that adiponectin content is inversely related to obesity. It can be seen from the data in Table 16 that the adiponectin content of the mice in the high-fat group was significantly lower than that of the normal group, and the four test groups of MATZHU and Matcha showed a significant effect of raising the serum ADP level in high-fat mice, among which the bitter bamboo-MATZHU and matcha with 2.5% added amount were better, and the ADP after intervention was close to that of the mice in the normal group.

Lipopolysaccharide (LPS) is mainly produced by the lysis of Gram-negative bacteria in the intestine. Studies have shown that lipopolysaccharide is closely related to the up-regulation of inflammatory factors expression in vivo of obese mice. The data in Table 16 shows that the lipopolysaccharide content of mice in the high-fat group was significantly higher than that of the normal group, and the test group added with MATZHU and matcha in the high-fat diet can significantly reduce the lipopolysaccharide level in the serum of obese mice, and the effect of 2.5% bitter bamboo-MATZHU was extremely significant, and the LPS value of this group of mice was significantly lower than that of the normal group. It shows that the dietary intervention of MATZHU and matcha can significantly improve the secretion of intracellular factors caused by high-fat diet.

Figure 9:
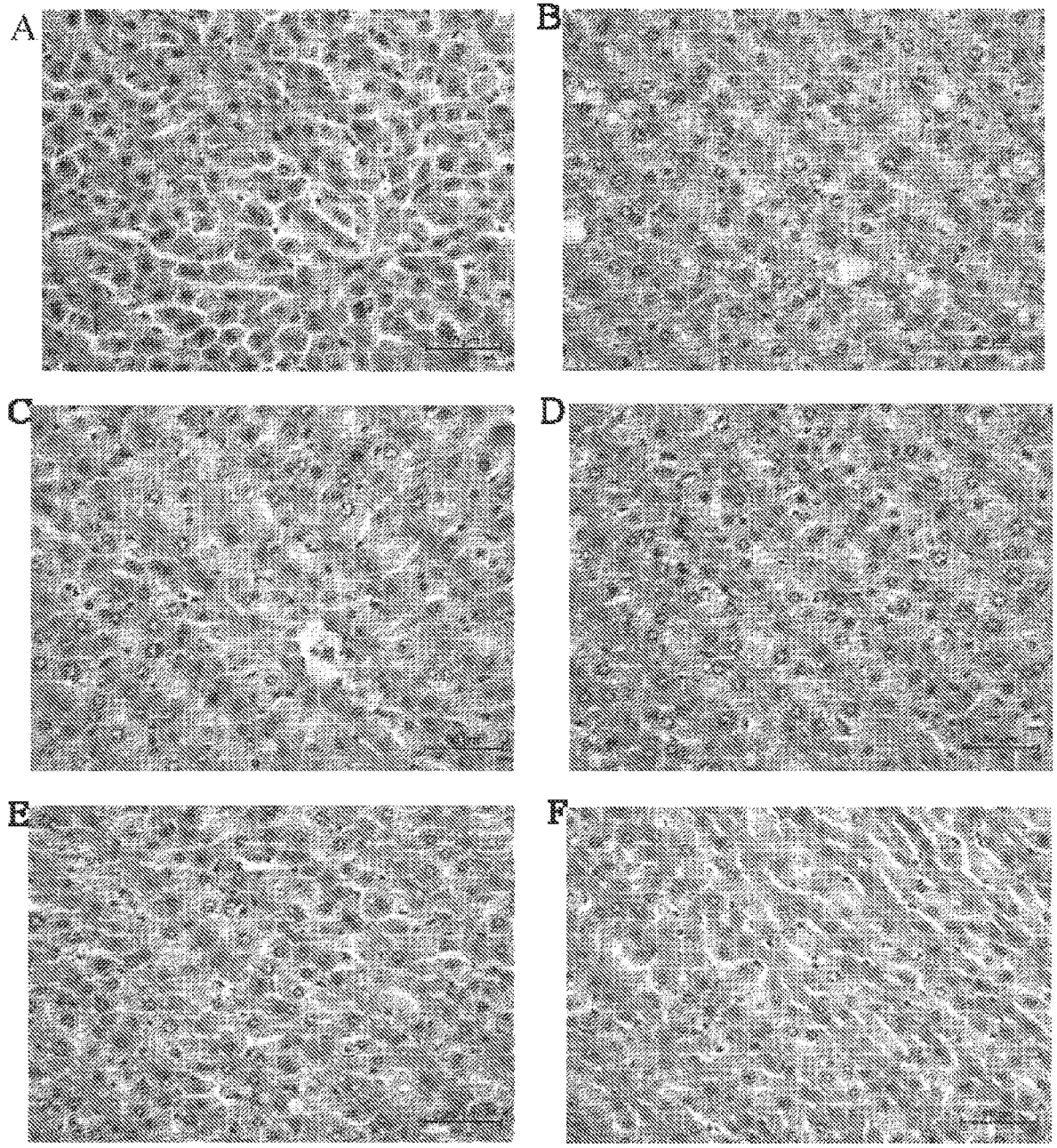
FIG. 9 shows H&E stained sections (400×) of liver of the experimental mice with metabolic syndrome, 50 μm. Wherein, A~E respectively represent that of normal group, high-fat group, 2.5% of bitter bamboo MATZHU+ high-fat group, 5.0% of bitter bamboo MATZHU+ high-fat group, 2.5% *Bashania fangiana* MATZHU+ high-fat group, and 2.5% matcha powder+high-fat group.

3.2.6 Effect of MATZHU and Matcha on Morphology of Liver and Fat Tissue of Experimental Mice FIG. 9 shows H&E stained sections of liver tissues of mouse in different groups. It can be seen that compared with normal group (A) mice, many white lipid droplets of different sizes appeared in liver sections of mice in high-fat model group (B), indicating that high-fat diet causes liver fat metabolism impaired, and the large amount of fat ingested cannot be decomposed successfully and gradually deposited in the liver. The number of liver fat droplets of the mice in the high-fat diet group (C, D, E) added with MATZHU and the high-fat diet group (F) added with matcha were significantly less than that in the high-fat model group, and there was no large white fat droplets. This shows that both MATZHU and matcha can significantly improve the lipid metabolism of the liver and reduce the risk of fatty liver caused by high-fat diet.

Figure 10:
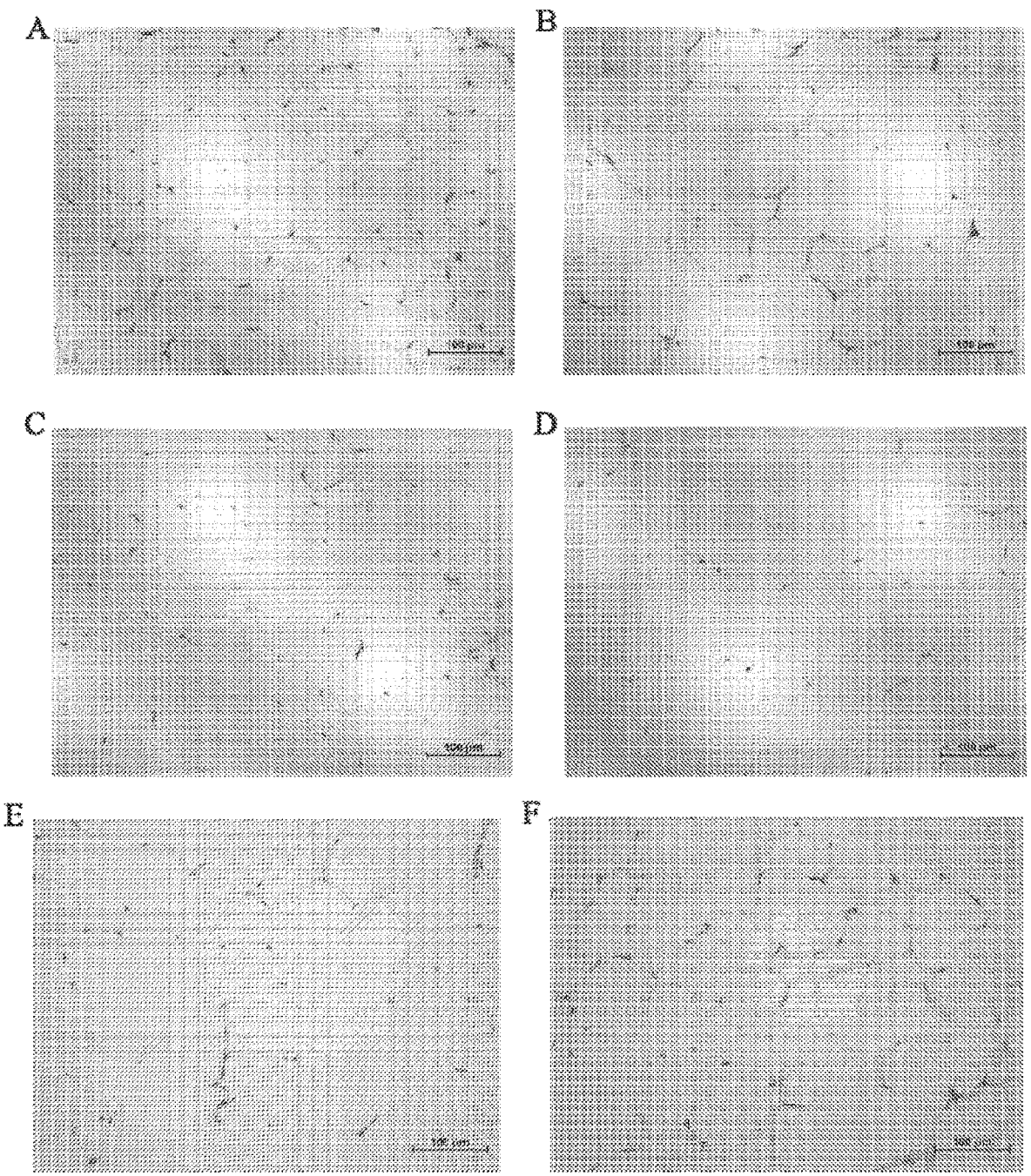
FIG. 10 shows H&E stained sections (200×) of adipose tissue of the experimental mice with metabolic syndrome, 100 μm. Wherein, A to E respectively represent that of the normal group, high-fat group, 2.5% of bitter bamboo MATZHU+ high-fat group, 5.0% of bitter bamboo MATZHU+ high-fat group, 2.5% of *Bashania fangiana* MATZHU+ high-fat group, and 2.5% matcha powder+high-fat group.

FIG. 10 shows H&E stained sections (200×) of epididymal adipose tissue of mice in different groups, where A to E respectively represent normal group, high-fat group, 2.5% bitter bamboo MATZHU+high-fat group, 5.0% bitter bamboo MATZHU+high fat group, 2.5% *Bashania fangiana* MATZHU+high fat group, and 2.5% matcha powder+high fat group. It can be seen from this that the mice in the high-fat model group (B) had a significantly larger fat cell volume than the normal group (A) due to long-term ingestion of high-fat feed. After the diet was fortified with MATZHU and matcha, the epididymal fat cells showed a significant reduction trend, and the 2.5% bitter bamboo-MATZHU group was the most significant.

3.2.7 Effect of MATZHU and Matcha on Intestinal Microflora in Experimental Mice

Figure 11:
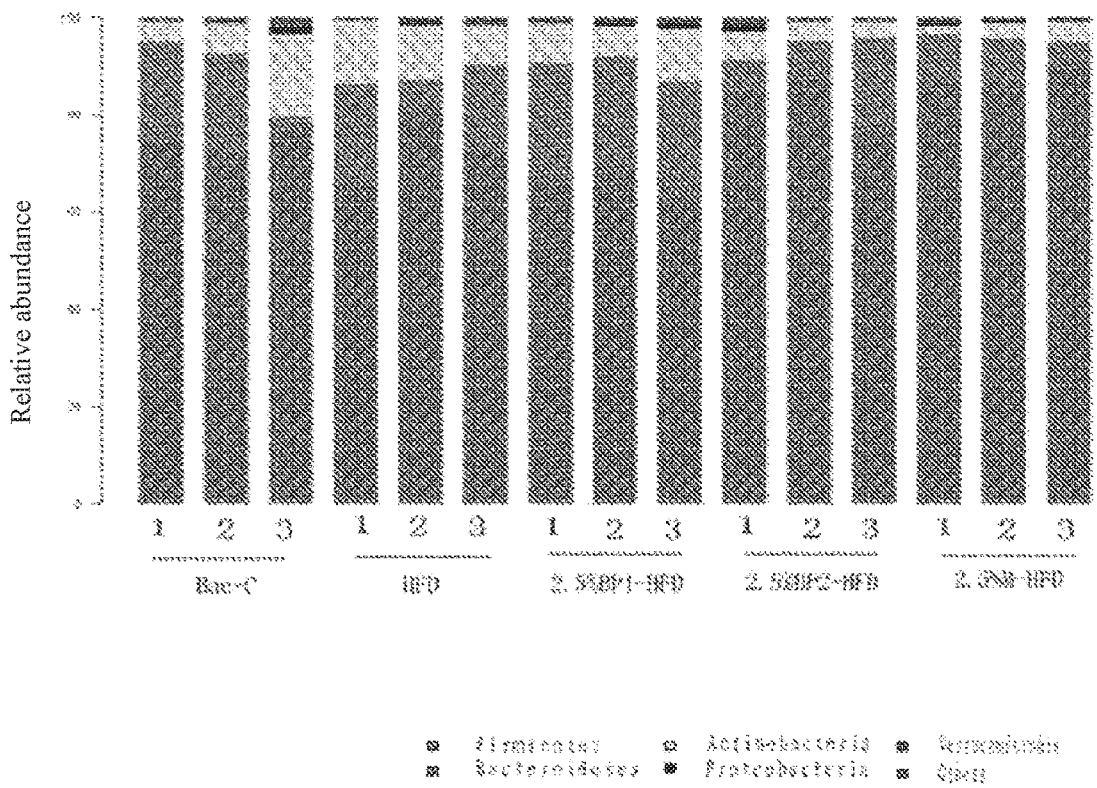
FIG. 11 shows a structure diagram of the intestinal flora of the experimental mice with metabolic syndrome.

The normal group, high-fat model group, added amount of 2.5% MATZHU and matcha test groups (bitter bamboo-MATZHU, *Bashania fangiana*-MATZHU and first-grade matcha) were selected, using high-throughput sequencing technology to analyze and determine the structures of the intestinal flora of these five groups of experiments mice, the result of which is shown in FIG. 11. In each column, from bottom to top are Firmicutes, Bacteroidetes, Actinobacteria, Proteobacteria and Verrucomicrobia.

Through high-throughput sequencing, OTUs of intestinal microorganisms of different groups of experimental mice were obtained. After gene library comparison and species annotation, it was found that the OUTs of the tested mice belonged to the following 9 gates: Firmicutes, Bacteroidetes, Actinobacteria, Proteobacteria, Deferribacteres, Verrucomicrobia, Cyanobacteria, Tenericutes and Saccharibacteria. Among them, the five gates, Firmicutes, Bacteroidetes, Actinobacteria, Proteobacteria, and Verrucomicrobia are common to all groups.

It can also be seen from FIG. 11 that in the intestinal microbes of the five groups of mice, the Firmicutes and Bacteroidetes dominate the absolute quantitative advantage. The research results of Professor Jeffrey I. Gordon from the University of Washington in the United States showed that the ratio of the abundance (F/B ratio) of Firmicutes and Bacteroidetes in the intestine of obese mice was significantly higher than that of thin mice. When the obese mice became thinner, their F/B value would decrease. The results of this study shows that the F/B value of mice in the high-fat model group (HFD) was 8.37, which was significantly higher than the F/B value of 3.58 in the normal group (Bac-C), and the F/B value of mice in the 2.5% bitter bamboo-MATZHU (BP1-HFD) group was significantly reduced to 2.82, indicating that it has a good regulating effect on the intestinal microflora structure of the mouse, which can correct the adverse effects caused by the high-fat diet. However, 2.5% of the *Bashania fangiana*-MATZHU and 2.5% matcha did not show this effect, and the F/B values of the two test groups did not decrease but increased instead, being 12.60 and 0.25, respectively.

EXAMPLE 4

Food Safety Evaluation of MATZHU (Acute Toxicity Test)

Twenty healthy and mature ICR mice with a weight of 18-22 g, 10 males and 20 females, were selected.

A dose group of 20.0 g/kg·BW according to the limit method were set. 20 g of henon bamboo-MATZHU was weighed and 40 mL sample liquid with 1% sodium carboxymethyl cellulose as solvent was prepared. The mice were fasted (without water deprivation) for 6 hours before gavage, and gavage was given at 20 mL/kg·BW. The mice were gavaged 2 times, with an interval of 4 hours each time. Three hours after the last gavage, they could eat and drink freely, and the animal's poisoning performance and death were recorded. The observation period was 14 days, and the body weight of mice at the beginning and end of the experiment period was recorded. The results are shown in Table 17.

TABLE 17

Acute toxicity test results of MATZHU in mice

| sex | starting weight(g) | final weight(g) | death (number of deaths/number of rats) | $LD_{50}$ (g/kg) |
|---|---|---|---|---|
| female | 20.5 ± 1.4 | 28.0 ± 1.4 | 0/10 | 20.0 |
| male | 20.4 ± 1.2 | 30.3 ± 1.3 | 0/10 | 20.0 |

During the acute toxicity test, none of the mice showed signs of poisoning and none died. It is concluded that the oral $LD_{50}$ of male and female mice for MATZHU is greater than 20.0 g/kg·BW, which is actually non-toxic.

EXAMPLE 5

Application of MATZHU in Food Industry 5.1 MATZHU Applied to Baked Food
5.1.1 Application of MATZHU in Cake Using bitter bamboo-MATZHU as a raw material, MATZHU chiffon cake was made according to the cake recipe in Table 18. The process for cake making is shown in FIG. 12.

TABLE 18

MATZHU chiffon cake recipe table

| raw material | egg white | egg yolk | white sugar | flour | MATZHU | baking powder | cake emulsifier | milk |
|---|---|---|---|---|---|---|---|---|
| weight/g | 120 | 70 | 48 in egg white 20 in egg yolk | 85 | 4.0% of flour | 2.5% of flour | 40 | 40 |

With the same recipe and production method, the MATZHU was replaced with matcha (Grade 1) to make matcha chiffon cake and ordinary cake. The sensory evaluation results comparing the sensory indicators of the three cakes are shown in Table 19.

TABLE 19

Sensory evaluation indexes of three cakes

| type | shape (20 points) | color (20 points) | internal structure (20 points) | taste (20 points) | elasticity (10 points) | specific volume (10 points) |
|---|---|---|---|---|---|---|
| ordinary cakes | 17.83 ± 1.11 [a] | 16.38 ± 1.26 [a] | 17.08 ± 1.26 [a] | 17.00 ± 1.73 [a] | 7.69 ± 0.75 [a] | 7.55 ± 0.16 [a] |
| MATZHU cakes | 18.17 ± 0.94 [a] | 17.23 ± 0.93 [a] | 16.92 ± 1.38 [a] | 15.69 ± 1.75 [ab] | 7.62 ± 0.87 [b] | 8.43 ± 0.09 [b] |
| matcha cakes | 14.42 ± 1.24 [b] | 12.46 ± 1.51 [b] | 14.38 ± 1.85 [b] | 14.69 ± 1.60 [b] | 5.77 ± 1.42 [a] | 7.99 ± 0.44 [c] |

15 sensory appraisers evaluated the 6 indicators of the three cakes respectively, with a total score of 83.5 points for ordinary cakes, 84.1 points for MATZHU cakes, and 69.7 points for matcha cakes. Among the three kinds of cakes, ordinary cakes and MATZHU cakes were more popular, except for the color, and the two had little difference in shape, elasticity and internal structure; and the specific volume of MATZHU and matcha cakes are higher. The above results indicate that MATZHU is more popular than matcha for making cakes, and its outstanding advantage is that it has a more green and attractive color.

5.1.2 Application in Cookies

Using bitter bamboo-MATZHU as a raw material, according to the raw material recipe of Table 20, a MATZHU cookie was prepared.

TABLE 20

Recipe of MATZHU cookies

| raw material | egg | berry sugar | powdered sugar | low-gluten flour | MATZHU | butter |
|---|---|---|---|---|---|---|
| weight/g | 1 | 30 | 50 | 200 | 4.0% of flour | 120 |

Preparation steps of MATZHU cookies: (1) Butter was put at room temperature until softened, whipped with egg beater until smooth.

(2) Fine granulated sugar and powdered sugar were added, and beat again until smooth, until the butter color became lighter, the volume became larger, and a smooth texture was formed.

(3) The broken egg liquid was added in three times, each time until it was fused, and then the next egg liquid was added. The butter volume at this time was fluffy, and the color was whitish like cream.

(4) Low-gluten flour and MATZHU were weighed, mixed well, then sieved into the whipped butter, stirred with a mixing spoon.

(5) The cookie batter was packed in a decorating bag, squeezed on a baking tray, and then baked under 180° C. for 15 minutes.

4.2 Application of MATZHU in Yogurt

Yili "Chang Qing" organic original flavored fermented milk was used as the base of MATZHU yoghurt, then added with 1.0% bitter bamboo-MATZHU and stirred evenly until no MATZHU particles can be seen. At the same time, matcha (first grade) yogurt with the same dosage was made. Then these two types of yogurt were compared with raw yogurt.

Twelve sensory appraisers were asked to evaluate the sensory sense of the three types of yogurt, including four evaluation indicators, color, flavor, tissue state and taste. The results are shown in FIG. 13. It can be seen from the figure that the matcha yoghurt scored the lowest among the four evaluation indicators. In terms of color and aroma, the matcha yoghurt scored slightly higher than that of ordinary yogurt. After added with the fresh green MATZHU, the color of the yoghurt also appeared bright green, which was easily loved by the public. In the evaluation of tissue state and taste, ordinary yogurt scored higher than that of MATZHU yogurt. In terms of tissue state, due to the addition of MATZHU and matcha powder, the scores of MATZHU yogurt and matcha yogurt were lower than that of raw yogurt.

The 12 sensory appraisers also chose the preference of the three yogurts, as shown in Table 21.

TABLE 21

Sensory appraisers' preference for three different yogurts

| sample | very like | like better | average | dislike | like degree |
|---|---|---|---|---|---|
| ①ordinary yogurt | 4 | 8 | 0 | 0 | 100% |
| ②MATZHU yogurt | 3 | 6 | 2 | 1 | 75% |
| ③matcha yogurt | 1 | 3 | 5 | 3 | 33.3% |

4.3 Application of MATZHU in Candy

The bitter bamboo-MATZHU was used in the production of nougat. The recipe is shown in Table 22, and the preparation method refers to the conventional technology.

TABLE 22

MATZHU nougat recipe

| raw material | milk powder | cotton candy | butter | MATZHU | peanut |
|---|---|---|---|---|---|
| weight/g | 50 | 100 | 20 | 5% of cotton candy | 35 |

In addition to MATZHU nougat, according to the same production process, ordinary nougat and nougat with the same concentration of matcha were produced. 15 sensory assessors sensed the four indicators, color, tissue state, flavor and taste, of the three types of nougat. The result is summarized in FIG. 14.

It can be seen from FIG. 14 that in terms of color, MATZHU nougat had the highest score, followed by plain nougat, and finally matcha nougat. In terms of tissue state, MATZHU nougat still scored slightly higher than the other two. In terms of flavor, the scores of the original flavor and the MATZHU flavor were very close, both higher than that of the matcha flavor. In terms of taste, the original nougat score was slightly higher than that of the other two. Due to the unique bitterness of matcha, it was difficult for some testers to accept.

To sum up, audience acceptance for MATZHU nougat was higher than that for matcha nougat.

4.4 Application of MATZHU in Seasoning Sauce

The bitter bamboo-MATZHU was used in the preparation of seasoning sauce, and the recipe is shown in Table 23.

TABLE 23

MATZHU sauce recipe table

| raw material | whole milk | whipped cream | sweetener | MATZHU | bacteriostatic agent |
|---|---|---|---|---|---|
| weight/g | 300 | 140 | 40 | 4.0% total sauce | 0.2 |

Preparation Steps of MATZHU Sauce:

(1) 100 g milk was heated to near boiling.

(2) The sieved MATZHU was added, mixed well with egg pump until smooth, to make a MATZHU milk solution.

(3) The remaining 200 g of milk, sweetener, and whipped cream were heated on a low heat to a viscous state, during which constant stirring was needed.

(4) The MATZHU milk solution was mixed with the viscous milk sauce in the previous step, and added with the bacteriostatic agent.
(5) Sterilized after packaging.

4.5 Application of MATZHU in Coffee

The henon bamboo-MATZHU was used to make solid beverages, and the recipe is shown in Table 24.

TABLE 24

Recipe of MATZHU solid beverage

| raw material | white granulated sugar | non-dairy powder | instant coffee powder | MATZHU |
|---|---|---|---|---|
| weight/g | 47.3 | 32.2 | 13 | 7.0% of total solid powder |

Method for Making MATZHU Solid Beverage:
Mixing all powders evenly and packaging them after passing the inspection.

4.6 Application of MATZHU in Noodles

The henon bamboo-MATZHU was used to make solid beverages, and the recipe is shown in Table 25.

TABLE 25

MATZHU noodle recipe

| raw material | flour | water | MATZHU |
|---|---|---|---|
| weight/g | 500 | 115 | 1.5% of total flour |

Preparation Steps of MATZHU Noodles:
(1) The sieved bamboo and 115 g water were mixed well into a slurry.
(2) The MATZHU pulp was added to the flour and mixed for 10 to 15 minutes.
(3) The dough was put into the noodle machine for rolling, drying, cutting, and packaging.

4.7 Application of MATZHU in Seasoning Salt

The bitter bamboo-MATZHU was used to make seasoning salt, and the formula is shown in Table 26.

TABLE 26

Formula table of MATZHU seasoning salt

| raw material | salt | bamboo leaf essence | MATZHU |
|---|---|---|---|
| weight/g | 80 | 0.024 | 0.3‰ of total salt |

Preparation Steps of MATZHU Seasoning Salt:
(1) 80 g of coarse salt was mixed with sieved MATZHU and bamboo leaf essence.
(2) The above mixture was grinded into a uniform powdered seasoning salt with a pulverizer.

EXAMPLE 5

MATZHU as a Dietary Supplement (Solid Beverage) Regulates the Body's Lipid Metabolism and Prevents Osteoporosis 5.1 Testing Method The bitter bamboo-MATZHU prepared in Example 1.6 was divided into small packages of 4 g/bag, which was eaten with warm water, or added with milk and honey water and stirred. Subjects were administered one sachet each morning and afternoon.

Eight males and eight females with varying degrees of obesity, abnormal lipid metabolism or insulin resistance were selected as the test population (age distribution between 30 and 64 years old, except for metabolic chronic disease, no other clinical disease indications), to be conducted with a 3-month trial. A total of 16 subjects were tested, the basic situation is listed in Table 27.

TABLE 27

Audiences for the MATZHU trial

| No | age (year old) | sex | height (cm) | starting weight (kg) | starting waist circumference (cm) | body mass index (BMI) | body weight |
|---|---|---|---|---|---|---|---|
| 1# | 56 | female | 158 | 60.5 | 81 | 24.23 | overweight |
| 2# | 38 | female | 158 | 78 | 113 | 31.24 | severe obesity |
| 3# | 35 | female | 152 | 57 | 81 | 24.67 | overweight |
| 4# | 51 | female | 161 | 51.7 | 73.3 | 19.95 | normal |
| 5# | 38 | female | 162 | 77 | 95 | 29.34 | overweight |
| 6# | 53 | female | 165 | 60.4 | 78 | 22.19 | normal |
| 7# | 51 | female | 161 | 68 | 85 | 26.23 | overweight |
| 8# | 63 | female | 164 | 78 | 89 | 29 | obesity |
| 9# | 30 | male | 174 | 80 | 95 | 26.42 | overweight |
| 10# | 33 | male | 178 | 80 | 86 | 25.25 | overweight |
| 11# | 47 | male | 175 | 83 | 92 | 27.10 | overweight |
| 12# | 40 | male | 171 | 77 | 88 | 26.33 | overweight |
| 13# | 42 | male | 177 | 88 | 90 | 28.09 | obesity |
| 14# | 53 | male | 169 | 83 | 98 | 29.06 | obesity |
| 15# | 56 | male | 167 | 77 | 86 | 27.61 | overweight |
| 16# | 60 | male | 166 | 72 | 88 | 26.13 | overweight |

During the test, the subjects maintained their original lifestyle, and the MATZHU was ingested as a dietary supplement. Fasting blood samples were taken before and after the test to detect blood lipid levels and bone density (ultrasound bone densitometer, left ankle). Body weight and waist circumference were recorded at the same time of every week, and various conscious symptoms during the test, such as appetite, sleep, mood, defecation, blood pressure, etc. were recorded.

5.2 Test Results 5.2.1 The Effect of MATZHU on Blood Fat and Body Fat

The changes in body fat and blood fat of 16 subjects before and after the 3-month test are shown in Table 28.

TABLE 28 the regulatory effect of MATZHU on body fat and blood fat

| No | body weight change (kg) | waist circumference change (cm) | BMI value change (Δ) | blood fat level change before and after the test (mmol/L) | | | | | | |
|---|---|---|---|---|---|---|---|---|---|---|
| | | | | TG | | TC | | HDL-c | | LDL-c | |
| | | | | before | after | before | after | before | after | before | after |
| 1# | −3.8 | −2.0 | −1.72 | 1.83↑ | 1.11 | 5.78↑ | 5.24 | 1.09 | 1.05 | 3.95↑ | 3.52 |
| 2# | −2.5 | −3.0 | −1.00 | 1.80↑ | 1.30 | 6.12↑ | 5.18 | 1.55 | 1.73 | 2.58 | 2.28 |
| 3# | −4.5 | −4.0 | −1.95 | 0.96 | 0.83 | 3.72 | 3.64 | 1.28 | 1.30 | 2.15 | 2.07 |
| 4# | −0.7 | −2.0 | −0.27 | 1.61 | 1.34 | 5.47 | 5.24 | 1.51 | 1.55 | 3.64 | 3.44 |
| 5# | −3.0 | −2.0 | −1.24 | 1.64 | 1.67 | 4.61 | 4.58 | 1.02 | 1.17 | 2.72 | 2.57 |
| 6# | −2.3 | −2.5 | −0.85 | 0.93 | 0.88 | 5.66↑ | 5.35 | 1.74 | 1.83 | 3.09 | 2.79 |
| 7# | −1.5 | −2.0 | +0.19 | 1.14 | 0.98 | 8.19↑ | 6.33↑ | 1.32 | 1.41 | 5.48↑ | 3.40 |
| 8# | −2.5 | −2.5 | −1.00 | 1.05 | 1.00 | 3.74 | 3.57 | 1.12 | 1.18 | 2.23 | 2.19 |
| 9# | −4.0 | −2.5 | −1.32 | 3.49↑ | 2.35↑ | 6.18↑ | 5.71 | 1.13 | 1.18 | 4.21↑ | 3.54 |
| 10# | −3.5 | −3.0 | −1.10 | 3.65↑ | 3.11↑ | 6.45↑ | 5.67↑ | 1.18 | 1.26 | 5.37↑ | 4.48↑ |
| 11# | −2.2 | −2.5 | −1.44 | 1.67 | 1.23 | 5.89↑ | 5.33 | 1.22 | 1.27 | 2.98 | 2.78 |
| 12# | −1.8 | −2.5 | −0.72 | 1.19 | 0.89 | 4.87 | 4.58 | 1.04 | 1.10 | 3.17 | 3.09 |
| 13# | −3.1 | −2.5 | −0.62 | 1.78 | 1.48 | 5.93↑ | 5.51 | 1.24 | 1.26 | 4.22↑ | 4.12 |
| 14# | −3.7 | −4.0 | −0.99 | 1.88↑ | 1.52 | 6.03↑ | 5.77 | 1.35 | 1.38 | 4.09↑ | 4.07 |
| 15# | −2.8 | −3.0 | −1.00 | 1.55 | 1.14 | 4.62 | 4.32 | 1.08 | 1.22 | 2.87 | 2.79 |
| 16# | −1.9 | −2.0 | −0.69 | 1.21 | 1.02 | 4.46 | 4.14 | 1.09 | 1.37 | 3.39 | 3.23 |

The data in Table 28 shows that the MATZHU has a significant regulating effect on the body fat and blood fat of the subjects. The weight loss of 16 test subjects was between 0.7 and 4.5 kg; and the waist circumference of all test subjects was reduced (2 to 4 cm), indicating that MATZHU had a certain effect on the reduction of centripetal fat in obese patients. At the same time, the levels of TG, TC and LDL-c of most testers showed a downward trend. Among them, abnormal serum TG and TC indicators of 1#, 2# and 14# subjects returned to normal levels after 3 months test. 7#, 9# and 10# dropped significantly. Except for 1# subject, the HDL-c of the other subjects increased to varying degrees, of which 2#, 15# and 16# had significant effects. In terms of LDL-c, LDL-c of 2#, 7#, 9# and 10# subjects decreased significantly to normal values. The above results all indicate that the intake of MATZHU as a dietary supplement can effectively regulate the fat metabolism of obese humans and plays a significant role in simultaneously reducing body fat and blood fat.

5.2.2 The Prevention and Treatment Effect of MATZHU on Osteoporosis

The changes in bone density of the above 8 subjects before and after the test are shown in Table 30. The results show that the rich minerals in MATZHU, especially the organic silicon and organic germanium, can effectively improve bone loss in middle-aged and elder people, especially for menopausal women.

TABLE 29

MATZHU's improvement of bone density in menopausal women

| No | age (year old) | bone density (g/cm$^2$) | |
|---|---|---|---|
| | | before the test | after the test |
| 1# | 56 | −3.1 | −1.8 |
| 2# | 38 | 1.1 | 1.5 |
| 3# | 35 | 2.5 | 2.8 |
| 4# | 51 | −1.8 | −0.8 |
| 5# | 38 | 1.5 | 2.0 |
| 6# | 53 | −1.8 | −0.8 |

TABLE 29-continued

MATZHU's improvement of bone density in menopausal women

| No | age (year old) | bone density (g/cm$^2$) | |
|---|---|---|---|
| | | before the test | after the test |
| 7# | 51 | −2.0 | −1.1 |
| 8# | 63 | −4.5 | −3.0 |

The invention uses fresh bamboo leaves as a raw material and adopts unique processing technology to create an superfine powder with excellent emerald color, delicate smell and uniform fineness, which is called MATZHU, which has the processing suitability and health effect close to matcha and provides a new type of natural, green food functional ingredients and/or dietary supplements rich in bamboo leaf chemicals and dietary fiber for the human society.

Finally, it should also be noted that the above list is only a few specific embodiments of the present invention. Obviously, the present invention is not limited to the above embodiments, and there can be many variations. All variations that can be directly derived from or associated with the disclosure of the present invention by those of ordinary skill in the art should be considered as the protection scope of the present invention.

The invention claimed is:

1. A method for preparing MATZHU, comprising the following steps:
   (1) blanching and color protecting raw materials;
   (2) drying the raw materials resulting from step (1) to obtain dried raw materials; and
   (3) superfine grinding the dried raw materials, to obtain the MATZHU having an average particle size of 1000-10,000 mesh;
   wherein the raw materials are leaves of Gramineae (Graminae) and Bambusoideae plant;
   wherein the blanching and color protecting step comprises: putting bamboo leaves as raw materials into a color-protecting solution with a temperature of 85 to 95° C., taking out after soaking for 30 to 90 seconds, and draining; and
   wherein the color-protecting solution used in the blanching and color protecting step is a zinc sulfate aqueous solution or a zinc gluconate aqueous solution or a combination thereof with a concentration of 0.5 to 2.0 g/100 mL.

2. The method of claim 1, wherein a material-to-liquid ratio of the bamboo leaf and the color protection liquid is 1 g: 50-100 mL.

3. The method of claim 1, wherein the drying of step (2) is drying the leaves after the blanching and color protecting step to a moisture content of ≤11%; and
   wherein the drying of step (2) uses at least one of hot air drying, microwave drying, vacuum drying and freeze drying.

4. The method of claim 1, wherein the source of the raw materials is fresh leaves of Zhejiang henon bamboo (*Phyllostachys meyeri* McClure), moso bamboo (*Phyllostachys heterocycla* var. *puhescens* (Mazel) Ohwi), *Neosinocalamus affinis* (*N.affinis* (Rendle) Keng f.) Mian bamboo (*B. intermedia* Hsueh et Yi), Sulfur Yu bamboo (*Yushania* Keng f.), bitter bamboo (*P. amarus* (keng) Keng f.), *Bashania fangiana* (*B.fangiana* Keng f. et Wen) and *sasa argenteastriatus* (*Pleiohlastus kongosanensis f.aureostriaus*).

5. The method of claim 1, wherein
   wherein the superfine grinding of step (3) comprises one of the following: high-energy nano-impact ball grinding, wherein the grinding ball is a zirconium ball, and ball-to-material ratio is 10:1; fluid energy grinding; or fluid energy grinding+high-energy nano-impact ball grinding.

* * * * *